US010449027B2

(12) United States Patent
Griffin et al.

(10) Patent No.: US 10,449,027 B2
(45) Date of Patent: Oct. 22, 2019

(54) DEPLOYMENT DEVICE FOR A SOFT TISSUE REPAIR PROSTHESIS

(71) Applicant: C.R. Bard, Inc., Murray Hill, NJ (US)

(72) Inventors: Jeremy Griffin, Providence, RI (US); Augustus Felix, Cranston, RI (US); John Conidi, Plainville, MA (US); Chris Bowley, Newport, RI (US); Marcus Stephen Papadopoulos, Paradise Valley, AZ (US); Daniel Joseph Greene, Chicago, IL (US)

(73) Assignee: C.R. Bard, Inc., Murray Hill, NJ (US)

( * ) Notice: Subject to any disclaimer, the term of this patent is extended or adjusted under 35 U.S.C. 154(b) by 150 days.

(21) Appl. No.: 15/386,939

(22) Filed: Dec. 21, 2016

(65) Prior Publication Data

US 2017/0181827 A1    Jun. 29, 2017

Related U.S. Application Data

(60) Provisional application No. 62/372,525, filed on Aug. 9, 2016, provisional application No. 62/271,896, filed on Dec. 28, 2015.

(51) Int. Cl.
*A61F 2/00* (2006.01)
*A61B 17/34* (2006.01)

(52) U.S. Cl.
CPC ........ *A61F 2/0063* (2013.01); *A61B 17/3468* (2013.01); *A61F 2002/0072* (2013.01); *A61F 2210/0076* (2013.01)

(58) Field of Classification Search
CPC ........ A61F 2/0063; A61F 2/2478–2481; A61F 2002/0068–0072; A61F 2002/2484; A61B 17/0057; A61B 2017/00575–00676
See application file for complete search history.

(56) References Cited

U.S. PATENT DOCUMENTS

| 5,258,000 A | 11/1993 | Gianturco |
| 5,366,460 A | 11/1994 | Eberbach |

(Continued)

FOREIGN PATENT DOCUMENTS

| EP | 1336391 A1 | 8/2003 |
| EP | 1336391 B1 | 12/2011 |

(Continued)

OTHER PUBLICATIONS

U.S. Appl. No. 16/138,321, filed Sep. 21, 2018, Pankratz et al.

*Primary Examiner* — Jonathan A Hollm
(74) *Attorney, Agent, or Firm* — Wolf, Greenfield & Sacks, P.C.

(57) ABSTRACT

A deployment device for positioning a soft tissue repair prosthesis includes a self-expanding support body releasably attachable to the prosthesis. The support body may be removably insertable into a pocket of the prosthesis. A handle coupled to the support body facilitates positioning the patch and/or removal of the support body from the pocket. The support body may substantially occupy the pocket in an expanded configuration. The handle may be arranged to direct a pulling force to the outer peripheral edge of the support body and/or cause a portion thereof to be pulled downward and below the body during withdrawal of the deployment device from the prosthesis. The support body may include support segments pivotally coupled together and foldable to collapse the support body for insertion into and removal from the pocket. One or more resilient support members may be provided for collapsing and expanding the support body and the prosthesis.

15 Claims, 27 Drawing Sheets

(56) References Cited

U.S. PATENT DOCUMENTS

| | | |
|---|---|---|
| 5,370,650 A | 12/1994 | Tovey et al. |
| 5,634,931 A | 6/1997 | Kugel |
| 5,769,864 A | 6/1998 | Kugel |
| 5,871,483 A | 2/1999 | Jackson et al. |
| 5,916,225 A | 6/1999 | Kugel |
| 6,132,470 A | 10/2000 | Berman |
| 6,171,318 B1 | 1/2001 | Kugel et al. |
| 6,174,320 B1 | 1/2001 | Kugel et al. |
| 6,290,705 B1 | 9/2001 | Chan et al. |
| 6,290,708 B1 | 9/2001 | Kugel et al. |
| 6,551,356 B2 | 4/2003 | Rousseau |
| 6,575,988 B2 | 6/2003 | Rousseau |
| 6,669,735 B1 | 12/2003 | Pelissier |
| 6,790,213 B2 | 9/2004 | Cherok et al. |
| 6,800,082 B2 | 10/2004 | Rousseau |
| 6,814,743 B2 | 11/2004 | Chin et al. |
| 7,101,381 B2 | 9/2006 | Ford et al. |
| 7,544,203 B2 | 6/2009 | Chin et al. |
| 7,785,334 B2 | 8/2010 | Ford et al. |
| 7,824,420 B2 | 11/2010 | Eldridge et al. |
| 7,947,062 B2 | 5/2011 | Chin et al. |
| 7,963,942 B2 | 6/2011 | Chen |
| 8,753,358 B2 | 6/2014 | Cook |
| 8,808,315 B2 | 8/2014 | Bailly et al. |
| 8,920,370 B2 | 12/2014 | Sholev et al. |
| 8,945,235 B2 | 2/2015 | Horton et al. |
| 9,005,223 B2 | 4/2015 | Cardinale et al. |
| 2001/0016754 A1 | 8/2001 | Adams et al. |
| 2004/0019360 A1 | 1/2004 | Farnsworth et al. |
| 2004/0073257 A1 | 4/2004 | Spitz |
| 2004/0087980 A1 | 5/2004 | Ford et al. |
| 2005/0043716 A1 | 2/2005 | Frimer |
| 2005/0192600 A1 | 9/2005 | Nicolo et al. |
| 2007/0299538 A1 | 12/2007 | Roeber |
| 2008/0147200 A1 | 6/2008 | Rousseau et al. |
| 2008/0237287 A1 | 10/2008 | Mitchinson |
| 2009/0082792 A1 | 3/2009 | Koyfman et al. |
| 2009/0270999 A1 | 10/2009 | Brown |
| 2009/0326676 A1 | 12/2009 | Dupic et al. |
| 2010/0069930 A1 | 3/2010 | Mitchell et al. |
| 2010/0241145 A1 | 9/2010 | Cook |
| 2011/0040311 A1 | 2/2011 | Levin et al. |
| 2011/0054500 A1 | 3/2011 | Levin et al. |
| 2011/0082479 A1 | 4/2011 | Friedlander |
| 2011/0144667 A1 | 6/2011 | Horton et al. |
| 2011/0224704 A1 | 9/2011 | Bailly et al. |
| 2011/0295283 A1 | 12/2011 | Darois et al. |
| 2013/0035704 A1 | 2/2013 | Dudai |
| 2013/0103058 A1 | 4/2013 | Gobran |
| 2013/0178876 A1 | 7/2013 | Horton et al. |
| 2013/0317527 A1 | 11/2013 | Jacinto et al. |
| 2014/0025093 A1 | 1/2014 | Horton et al. |
| 2014/0051915 A1 | 2/2014 | Sholev et al. |
| 2014/0316444 A1* | 10/2014 | Pankratz ............... A61F 2/0063 606/151 |
| 2015/0257866 A1 | 9/2015 | Filipiak et al. |
| 2017/0181828 A1 | 6/2017 | Felix et al. |
| 2017/0181829 A1 | 6/2017 | Felix et al. |
| 2017/0181830 A1 | 6/2017 | Felix et al. |
| 2018/0206968 A1 | 7/2018 | Pankratz et al. |
| 2019/0021832 A1 | 1/2019 | Pankratz et al. |

FOREIGN PATENT DOCUMENTS

| | | |
|---|---|---|
| EP | 2543339 A1 | 1/2013 |
| WO | WO 2011/043795 A1 | 4/2011 |
| WO | WO 2011/128903 A2 | 10/2011 |
| WO | WO 2013/148839 A1 | 10/2013 |
| WO | WO 2015/104014 A1 | 7/2016 |

* cited by examiner

DEPLOYMENT DEVICE FOR A SOFT TISSUE REPAIR PROSTHESIS

FIELD

A deployment device for a soft tissue repair prosthesis.

BACKGROUND

A hernia defect is an opening or weakness in a tissue or muscle wall, such as the abdominal wall. One approach for repairing a hernia is to cover the tissue or muscle wall defect with a patch of repair fabric. The patch may be placed in an open procedure or through a minimally invasive procedure, such as by a laparoscopic technique.

In a hernia repair procedure, a patch may be delivered through a surgical incision to a treatment site within the patient. Because the patch is typically larger than the pathway to the surgical site, the patch may be reduced in size to enable passage through the surgical opening into the patient. After deployment at the treatment site, the patch needs to return to an enlarged shape sufficient to cover the defect. Certain hernia repair patches include a resilient support member, such as an elastic filament, that is collapsed along with the patch into a reduced configuration and delivered through the surgical opening. After delivery through the incision, the resilient support member opens, such as by unfurling if rolled into the reduced configuration, causing the associated patch to expand into the enlarged repair configuration. The expanded patch including the resilient support member is then fixated to the tissue or muscle wall over the defect.

SUMMARY

According to one aspect, a deployment device for a soft tissue repair prosthesis comprises a self-expanding support body and a handle coupled to the support body. The support body is to be releasably coupled to the soft tissue repair prosthesis to assist in spreading the soft tissue repair prosthesis from a reduced configuration to an expanded configuration. The support body is collapsible from an expanded configuration to a reduced configuration. The handle includes a distal end and a free end opposite the distal end. The distal end of the handle is coupled to the support body to position the soft tissue repair prosthesis relative to a soft tissue defect when the support body is coupled to the soft tissue repair prosthesis and to release the support body from the soft tissue repair prosthesis with a pulling force on the free end of the handle in an outward direction away from the soft tissue repair prosthesis when the soft tissue repair prosthesis is in the expanded configuration. The distal end of the handle is coupled to a portion of the support body to apply the pulling force and collapse the portion of the support body in an inward direction toward the soft tissue repair prosthesis. The support body is manipulable into the reduced configuration with the soft tissue repair prosthesis for insertion through a surgical opening into a patient.

According to another aspect, a method is provided for repairing a hernia defect. The method comprises an act of (a) delivering a prosthesis in a reduced configuration through a surgical opening into a patient. The prosthesis includes a patch body and a deployment device. The deployment device includes a self-expanding support body and a handle coupled to the support body. The support body is releasably coupled to the patch body to assist in spreading the patch body to an expanded configuration. The method further comprises acts of: (b) following act (a), spreading the patch body to the expanded configuration via the support body, (c) securing the patch body in the expanded configuration about the hernia defect, (d) following act (c), removing the support body from the pocket of the patch body by directing an outward pulling force applied with the handle to a location at or in close proximity to an outer periphery of the support body to collapse a portion of the support body inwardly toward the patch body, and (e) withdrawing the deployment device through the surgical opening out of the patient.

According to another aspect, a deployment device for a soft tissue repair prosthesis comprises a self-expanding support body and a handle coupled to the support body. The support body is to be releasably coupled to the soft tissue repair prosthesis to assist in spreading the soft tissue repair prosthesis from a reduced configuration to an expanded configuration. The support body includes an outer peripheral edge and an opening extending therethrough to facilitate collapse of the support body from an expanded configuration to a reduced configuration. The handle includes a distal end coupled to the support body and a free end extendable away from the support body. The handle is coupled to position the soft tissue repair prosthesis relative to a soft tissue defect when the support body is coupled to the soft tissue repair prosthesis and to release the support body from the soft tissue repair prosthesis with a pulling force on the free end of the handle in an outward direction away from the soft tissue repair prosthesis when the soft tissue repair prosthesis is in the expanded configuration. The distal end of the handle is coupled to the support body to direct the pulling force to the outer peripheral edge of the support body. The support body when coupled to the soft tissue repair prosthesis is manipulable into the reduced configuration with the soft tissue repair prosthesis for insertion through a surgical opening into a patient.

According to another aspect, a method is provided for repairing a hernia defect. The method comprises an act of: (a) delivering a prosthesis in a reduced configuration through a surgical opening into a patient. The prosthesis includes a patch body and a deployment device. The deployment device includes a self-expanding support body and a handle coupled to and extending away from the support body. The support body is releasably coupled to the patch body to assist in spreading the patch body to an expanded configuration. The support body includes an outer peripheral edge and an opening extending therethrough to facilitate collapse of the support body for removal through the surgical opening. The method further comprises acts of: (b) following act (a), spreading the patch body to the expanded configuration via the support body, (c) securing the patch body in the expanded configuration about the hernia defect, (d) following act (c), removing the support body from the pocket of the patch body by directing a pulling force applied with the handle to a location at or in close proximity to the outer peripheral edge of the support body to collapse the support body, and (e) withdrawing the deployment device through the surgical opening out of the patient.

According to another aspect, a deployment device for a soft tissue repair prosthesis comprises a self-expanding support body and a handle coupled to the support body. The support body is to be releasably coupled to the soft tissue repair prosthesis to assist in spreading the soft tissue repair prosthesis from a reduced configuration to an expanded configuration. The handle includes a distal end coupled to the support body and a free end extendable away from the support body. The support body includes a first support segment and a second support segment, the first and second support segments pivotally coupled together to collapse the support body from an expanded configuration to a reduced configuration. The handle is coupled to the support body to position the soft tissue repair prosthesis relative to a soft tissue defect when the support body is coupled to the soft tissue repair prosthesis and to release the support body from the soft tissue repair prosthesis with a pulling force on the free end of the handle in an outward direction away from the soft tissue repair prosthesis when the soft tissue repair prosthesis is in the expanded configuration. The support body when coupled to the soft tissue repair prosthesis is manipulable into the reduced configuration with the soft tissue repair prosthesis for insertion through a surgical opening into a patient.

According to another aspect, a method is provided for repairing a hernia defect. The method comprises an act of: (a) delivering a prosthesis in a reduced configuration through a surgical opening into a patient. The prosthesis includes a patch body and a deployment device. The deployment device includes a self-expanding support body and a handle coupled to and extending away from the support body. The support body is releasably coupled to the patch body to assist in spreading the patch body to an expanded configuration. The support body includes a first support segment and a second support segment. The first and second support segments are pivotally coupled together to collapse the support body for removal through the surgical opening. The method further comprises acts of: (b) following act (a), spreading the patch body to the expanded configuration via the support body, (c) securing the patch body in the expanded configuration about the hernia defect, (d) following act (c), collapsing the support body from an expanded configuration to a reduced configuration, (e) releasing the collapsed support body from the patch body, and (f) withdrawing the deployment device through the surgical opening out of the patient.

According to another aspect, a deployment device for a soft tissue repair prosthesis comprises a self-expanding support body and a handle coupled to the support body. The support body is to be releasably coupled to the soft tissue repair prosthesis to assist in spreading the soft tissue repair prosthesis from a reduced configuration to an expanded configuration. The support body is collapsible from an expanded configuration to a reduced configuration. The support body includes a first support segment and a second support segment which are coupled together in an alternating overlap arrangement. The handle includes a distal end and a free end opposite the distal end. The distal end of the handle is coupled to the support body to position the soft tissue repair prosthesis relative to a soft tissue defect when the support body is coupled to the soft tissue repair prosthesis and to release the support body from the soft tissue repair prosthesis with a pulling force on the free end of the handle in an outward direction away from the soft tissue repair prosthesis when the soft tissue repair prosthesis is in the expanded configuration. The support body is manipulable into the reduced configuration with the soft tissue repair prosthesis for insertion through a surgical opening into a patient.

According to another aspect, a deployment device for a soft tissue repair prosthesis comprises a self-expanding support body and a handle coupled to the support body. The support body is to be releasably coupled to the soft tissue repair prosthesis to assist in spreading the soft tissue repair prosthesis from a reduced configuration to an expanded configuration. The support body includes a first support segment and a separate second support segment which are coupled together to collapse the support body from an expanded configuration to a reduced configuration. The first support segment includes a first resilient support member and the second support segment includes a second resilient support member. The first and second support members support the support body in the expanded configuration. The handle includes a distal end and a free end opposite the distal end. The distal end of the handle is coupled to the support body to position the soft tissue repair prosthesis relative to a soft tissue defect when the support body is coupled to the soft tissue repair prosthesis and to release the support body from the soft tissue repair prosthesis with a pulling force on the free end of the handle in an outward direction away from the soft tissue repair prosthesis when the soft tissue repair prosthesis is in the expanded configuration. The support body is manipulable into the reduced configuration with the soft tissue repair prosthesis for insertion through a surgical opening into a patient.

According to another aspect, a deployment device for a soft tissue repair prosthesis comprises a self-expanding support body and a handle coupled to the support body. The support body is to be releasably coupled to the soft tissue repair prosthesis to assist in spreading the soft tissue repair prosthesis from a reduced configuration to an expanded configuration. The support body is collapsible from an expanded configuration to a reduced configuration. The handle includes a distal end coupled to the support body and a free end opposite the distal end. The handle further includes an intermediate portion between the distal end and the free end that is releasably securable to the support body to position the soft tissue repair prosthesis relative to a soft tissue defect when the support body is coupled to the soft tissue repair prosthesis. The support body is releasable from the soft tissue repair prosthesis with a pulling force on the free end of the handle in an outward direction away from the soft tissue repair prosthesis when the intermediate portion of the handle is released from the support body and the soft tissue repair prosthesis is in the expanded configuration. The support body is manipulable into the reduced configuration with the soft tissue repair prosthesis for insertion through a surgical opening into a patient.

BRIEF DESCRIPTION OF DRAWINGS

Aspects of the invention are described below, by way of example, with reference to the accompanying drawings in which like numerals reference like elements, and wherein.

DETAILED DESCRIPTION

Figure 1:
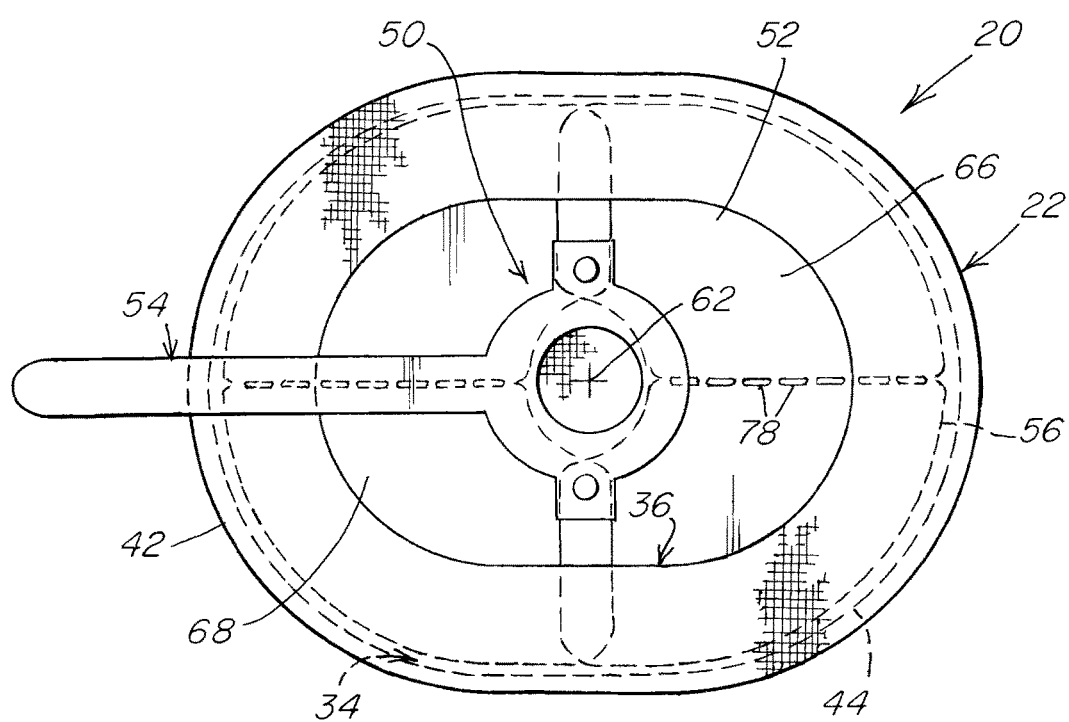
FIG. 1 is an illustration of a prosthesis for repairing a hernia defect with an assembled hernia repair patch and deployment device in an expanded configuration.

It should be understood that aspects of the invention are described herein with reference to certain illustrative embodiments and the figures. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

Various embodiments are described in connection with the repair of a hernia, specifically a ventral hernia. However, the invention is not necessarily so limited, and may be employed to repair other types of hernias, other soft tissue or muscle wall defects, as well as may be used in other surgical or medical treatments. With respect to repair of a ventral hernia, the repair patch may be placed in the intraperitoneal, preperitoneal, retromuscular, or other anatomical space, as the invention is not so limited. For ease of understanding, the hernia repair patch is described in connection with an open repair procedure but may be employed in minimally invasive procedures, or in other techniques for repairing a hernia or other soft tissue defect as should be apparent to one of skill in the art.

A patch for repairing a hernia may include a patch body having a first side that will be positioned against a tissue or muscle wall, such as the abdominal wall, that includes the defect. The first side of the patch body may be configured for tissue ingrowth. Where the patch will be located adjacent sensitive organs, such as the intestines or other viscera, an opposite second side of the patch body may include a barrier, such as a layer of barrier material or a barrier coating, to prevent adhesions between the first side of the patch and the sensitive organs. Alternatively, the second side of the patch body may also be configured for tissue ingrowth.

The patch body may include a pocket to facilitate positioning and/or fixation of the patch relative to the hernia defect. The pocket may be accessible through an access opening in the patch body. The patch body may include multiple layers of biocompatible material with the pocket formed between adjacent layers. The access opening may be provided in one of the layers forming the pocket. The layer with the access opening may have, but is not limited to, an annular configuration.

In some open procedures, a hernia repair patch may be reduced in size to facilitate delivery of the prosthetic device to the treatment site. For example, a hernia repair patch may be rolled into a cylindrical shape, or otherwise collapsed into a smaller configuration, suitable for passage through a surgically created opening, such as an incision. After delivery to the surgical site, the reduced hernia repair patch is transformed into an expanded configuration. The enlarged patch is then placed against the abdominal wall and may be fixated by sutures, staples, tacks and/or other fixation elements. For example, fixation elements may be applied through a border region adjacent the outer peripheral edge, and/or at other locations, of the patch into healthy tissue surrounding the defect. For some procedures, the patch may include an accessible pocket which extends to the border region. The fixation elements may be delivered through the pocket and positioned at the border region for fixation to tissue surrounding the defect. A surgical instrument, such as a suturing device, stapler or tacker, may be inserted into the pocket and positioned at desired locations along the outer periphery of the pocket to apply a fixation element through the border region of the patch.

A deployment device may be employed to position and provisionally hold the expanded patch against the abdominal wall pending fixation. The deployment device may include a support body configured to be releasably coupled to the patch body. For applications that employ a patch body with a pocket, the support body may be configured to be removably inserted in the pocket of the patch. For applications that employ a patch body without a pocket, one or more releasable fixating components may be employed for releasably connecting the support body to the patch body. For example, and without limitation, the releasable fixating components may include a coil-type fixating component located at various locations about the support body. The coil-type fixating component may have an extended, linear configuration that facilitates passing the fixating component into, and removing the fixating component from, the patch body and a retracted, coiled configuration which retains the patch body. Other arrangements for releasably attaching the support body to the patch body also are contemplated. For example, and without limitation, a suture may run between the support body and the patch body. The suture can be cut at one or more locations and then the support body pulled away from the patch body. Alternatively, the suture may be sufficiently weak or be modified to include one or more localized weak points that will fail upon application of a sufficient pulling force. Alternatively, the support body may be adhered by a relatively weak adhesive to the patch body. Another option is to configure the support body and/or patch body so as to releasably engage each other. In one such arrangement, the patch body may include one or more slits that releasably receive an aspect of the support body.

For applications that employ a patch body with a pocket, the support body may have a size and shape that generally corresponds with the size and shape of the pocket. Alternatively, the support body may have a size and shape that differs from the size and/or shape of the pocket. For example, the pocket could be rectangular and the support body oval. Representative shapes of a support body include, but are not limited to, circular, oval or a polygon. In one embodiment, the deployment device includes a generally oval self-expanding support body that is insertable into a generally oval pocket.

In an expanded configuration, the support body is larger than the access opening to the pocket and extends across a substantial portion of the pocket to maneuver the patch body into position. In a collapsed configuration, the support body may be inserted into or removed from the pocket through the access opening. To reduce movement between the deployment device and the patch body, the support body may have an outer peripheral edge that is located in close proximity to and generally follows the outer periphery of the pocket when the support body is inserted and expanded in the pocket. The support body may be compliant to facilitate its collapsibility when inserted into and removed from the patch pocket, and when the assembled patch and deployment device are rolled up or otherwise reduced in shape for delivery to the treatment site.

The support body may be configured as a shield to help protect underlying tissue and/or adjacent organs, such as the intestines or other viscera, from unintentional penetration by the fixation elements during fixation of the patch about the hernia defect. In this manner, the support body may have a generally planar configuration that is sized and shaped to occupy a substantial portion of the pocket. When inserted into the pocket, a surgical instrument may be moved along a surface of the support body into position for delivering a fixation element. The support body may be constructed of material that is difficult to penetrate with fixation tools and fixation elements. The material of the support body may also have a lubricity that facilitates sliding a fixation tool along the surface into position, as well as facilitate insertion and withdrawal of the support body into and from the patch.

A handle may extend from the support body and be passed through the access opening to the pocket of the patch body, if provided, so that a free end of the handle is accessible on the side of the patch body facing the surgical incision. When the assembled patch and deployment device have unfurled or otherwise opened to an expanded shape at the surgical site, the handle may be drawn through the surgical incision to outside of the patient. The handle may be manipulated to position and draw the support body, and the patch body supported by the support body, over the hernia defect and upwardly against the abdominal wall. The handle may be adjustable and/or flexible but be sufficiently stiff to control movement and/or allow manipulation of the support body for positioning the patch relative to the hernia defect. The handle may be pivotal and/or rotatable to various positions relative to the support body.

The handle may be arranged to apply a pulling force to one or more selected regions of the support body. For example, and without limitation, the handle may apply a pulling force to a central region, an outer peripheral region, and end region, or any other region of the support body suitable for positioning, manipulating and/or collapsing the support body as should be apparent to one of skill in the art.

The handle may be releasably attachable to a portion of the support body to facilitate movement and/or manipulation of the support body and the patch. For example, and without limitation, an intermediate portion of a handle arranged to direct a pulling force to an outer peripheral or end region of the support body may be configured to be releasably attached to a central region of the support body. In this manner, when the intermediate portion of the handle is attached to the support body, a pulling force on the handle will be directed toward the central region of the support body to position and/or manipulate the support body and the patch. When the handle is released, the pulling force on the handle will be directed toward the outer peripheral or end region of the support body to facilitate removal of the support body from the patch.

The deployment device may be provided with one or more features that assist with collapse of the support body and/or the handle to facilitate collapsing the deployment device for insertion into and/or removal from the pocket. For example, and without limitation, the features may permit portions of the support body and/or the handle to pivot, fold, slide and/or overlap as the deployment device is collapsed to a smaller configuration for insertion into and removal from the pocket of the patch body.

According to one aspect, the support body may include support segments pivotally coupled together to facilitate collapse of the support body for insertion into and removal from the pocket. The support segments may be coupled along an overlap region between the segments. An alternating overlap arrangement may be employed along the overlap region.

The support body may have a generally planar configuration in the expanded configuration which may be collapsed to a non-planar configuration for insertion into and removal from the pocket. For example, and without limitation, the support body may be collapsed to a generally flattened trapezoidal configuration or a generally conical or frusto-conical configuration. The support segments may be configured to fold, bend or flex as the segments pivot relative to each other to further facilitate collapse of the support body. The segments may fold, bend or flex about a first axis and the segments may pivot about one or more axes located in a plane that is perpendicular to the first axis. The segments may include one or more reliefs and/or preformed fold lines to facilitate folding or bending.

The handle may be coupled to a region, such as a central region, of the support body so that a pulling force on the handle causes the support body to collapse into a generally flattened trapezoidal configuration or a generally conical or frusto-conical configuration with portions of the support segments overlapping each other, such as a petal-like configuration. The handle may also be configured to fold, bend or flex to facilitate collapsing the deployment device. Such an arrangement may reduce the pulling force required to release the deployment device from the patch body, such as remove it from the pocket of the patch body, with minimal, if any, spraying of bodily fluids as the deployment device is withdrawn from the surgical site through the surgical opening.

According to another aspect, the support body may employ a single piece structure for insertion into and removal from the pocket. The handle may be arranged to direct a pulling force at or in proximity to an outer peripheral edge at an end of the support body along a first axis. The handle may extend from a location outside, at or in proximity to the outer peripheral edge at the end of the support body. Alternatively, the handle may extend from a location spaced inwardly from the outer peripheral edge. A portion of the handle may extend through the support body at a location inwardly from the outer peripheral edge.

The single piece structure may be provided with an opening extending therethrough to facilitate collapse of the support body. A radial slit may extend from the opening to the outer peripheral edge of the support body. The slit may extend along a first axis to a first end of the support body. The edges of the support body defining the slit may substantially abut along the length of the slit to provide a substantially continuous planar surface across the support body.

A pulling force on the handle causes the support body to collapse from a generally planar configuration to a non-planar configuration. For example, and without limitation, the support body may be collapsed to a non-conical configuration. The handle may be arranged to pull the end of the support body outwardly away from the patch body. Alternatively, the handle may be arranged to draw the end of the support body down or inwardly toward the patch body so as to tuck the end portion below the support as it is removed from the patch. If provided with an opening and radial slit, the support body may be collapsed to a non-conical configuration with portions of the support body along the slit overlapping each other. Such arrangements may reduce the pulling force required to remove the deployment device from the pocket of the patch body with minimal, if any, spraying of bodily fluids as the deployment device is withdrawn from the surgical site.

A force translation component may be provided to translate the pulling force from the handle to a region of the support body from the outer peripheral edge at the second end toward a central region of the support body or the opening, if provided. The force translation component may be located along the first axis on a side of the support body opposite the handle, and may extend from a location outside the peripheral edge to a location proximate the central region or opening. One or more separate grips may be provided to facilitate positioning the patch body relative to the hernia defect. The grips may be located in the central region or between the opening, if provided, and the second end of the support body.

The support body may have a relatively thin, planar shape in the expanded configuration to facilitate collapsing the patch and deployment device into a reduced size, such as by rolling them into a cylindrical shape, for delivery to the hernia repair site. To assist in unfurling the patch into an expanded shape after deployment, the support body may have a resiliency or other property (e.g., shape memory) that allows the support body to deform from an initial, expanded, shape into a compact configuration as the patch is reduced in size for delivery through the surgical opening, and then return to the initial shape, or at least to a shape larger than the reduced shape, upon reaching the delivery site. Such an ability to revert from a collapsed or reduced configuration to an expanded configuration without requiring assistance of a medical professional is referred to herein as a "self-expanding" support body. Recovery of the support body causes the patch to spread out into an expanded configuration.

The support body may be formed from one or multiple layers of material including, but not limited to, nylon, polytetrafluoroethylene (PTFE), polyethylene terephthalate glycol (PETG), polypropylene, and polyethylene. It is also contemplated that the support body may be formed of an elastomeric material including, but not limited to, silicone.

According to one aspect, the support body may include one or more resilient support members, including frame structures, which permit collapse of the support body and the patch into a reduced configuration and then assist in expanding the support body and the patch. The frame(s) may be sandwiched between separate layers of material that form the support segments of the support body or the single piece structure of the support body. For example, and without limitation, the support body may be formed from two layers of nylon material that sandwich a support frame formed of PETG. The frame(s) may have, but are not limited to, an annular configuration that extends about and follows the contour of the outer periphery of the support segments or the support body.

According to another aspect, the support body may be formed of a material that alone provides a desired balance of flexibility, stiffness and resilience for allowing the support body to be collapsed and expanded while providing support for the patch. For example, and without limitation, the support body may include a laminated sheet formed from multiple layers of PTFE material. The number, thickness and/or orientation of individual layers relative to each other may be selected to provide the laminated sheet with desired properties for flexibility, stiffness and/or resilience.

The support body may be characterized by its positioning relative to the axes of the patch body. For example, the support body may include a top portion that is positionable on an upper portion of the patch body relative to a first axis, and a bottom portion that is positionable on an opposite, lower portion of the patch body relative to the first axis. Each of the top portion and the bottom portion of the support body may have a curved profile, although straight, compound straight, angled and/or curved, and other profiles are contemplated as should be apparent to one of skill in the art. The support body may include lateral and medial portions which may have similar or different profiles as compared to the top and bottom portions.

With the patch body spread out over the hernia defect, and secured to the tissue or muscle wall, the inventors have recognized that there no longer is need for the deployment device. Accordingly, the support body, as observed earlier, may be releasably coupled to the hernia repair patch, such as by being removably inserted in a pocket of the hernia repair patch, allowing selective removal of the deployment device by the surgical team after expanding, positioning, and/or fixation of the patch body. Removal of the support body from the pocket of the patch will, in turn, separate the deployment device from the fixated patch body. The detached deployment device may then be removed from the patient, such as by withdrawal through the same opening in which the patch and deployment device had been delivered into the patient. Withdrawal may be facilitated by collapsing the support body and/or portions of the handle at one or more regions and pulling a free end of the handle to draw the support body and handle into a collapsed configuration that may readily pass through the opening used for delivering the patch and deployment device. The support body and/or handle may be configured and arranged to reduce the pulling force required to remove the deployment device from the pocket of the patch body with minimal, if any, spraying of bodily fluids as the deployment device is withdrawn from the surgical site through the surgical opening.

Figure 2:
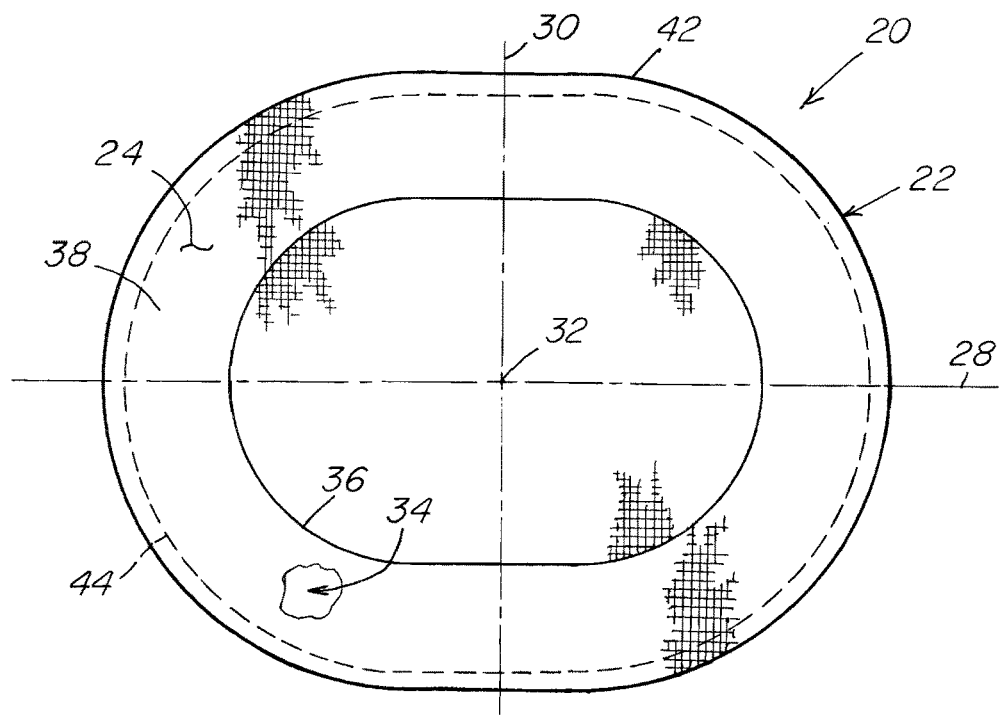
FIG. 2 is a top view of a hernia repair patch.
Figure 3:
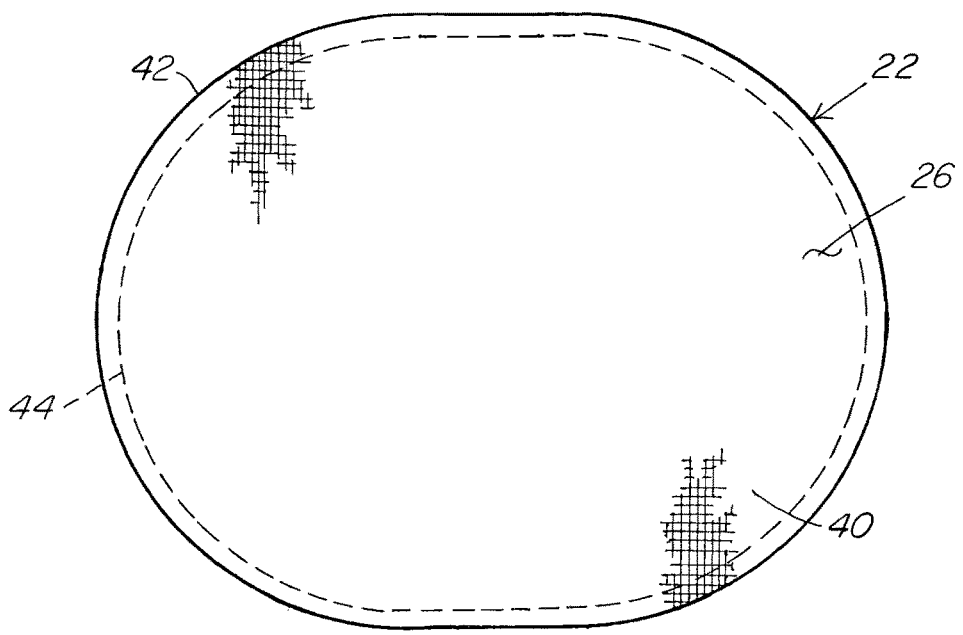
FIG. 3 is a bottom view of the hernia repair patch of FIG. 2.

As shown in FIGS. 1-3, a prosthesis 20 for repairing a hernia or other soft tissue defect may include a patch body 22 having a first surface 24 configured to face the hernia defect and a second surface configured to face away from the hernia defect. The first surface 24 may be arranged for tissue ingrowth, and may include one or more tissue infiltratable layers such as a mesh or other porous fabric amenable to tissue ingrowth. The second surface 26 may also be arranged for tissue ingrowth, and may include a tissue infiltratable layer such as a mesh or other porous fabric amenable to tissue ingrowth. Alternatively, the second surface may be configured as a barrier to adhesions between the first surface and sensitive organs or tissue, such as the intestines or other viscera. The second surface may be a solid or substantially non-porous barrier layer or a barrier coating that will prevent contact between the viscera and the porous tissue ingrowth fabric. As shown in FIG. 2, the patch body 22 may be defined by a first axis 28 and a second axis 30 that is substantially perpendicular to the first axis. The intersection of the first and second axes may coincide with a center, or approximate center 32, of the patch body.

In one embodiment, the patch body may include a pocket 34 and an access opening 36 to the pocket to facilitate positioning and securement of the patch body 22 relative to a hernia defect. The pocket may be located between the first and second surfaces of the patch body. In one embodiment, the pocket 34 may be formed with a first layer 38 and a second layer 40 of biocompatible material connected to each other, such as by stitching or welding, at or proximate to the outer peripheral edge 42 of the patch body. The outer periphery 44 of the pocket may be in close proximity to and extend along the connection between the layers. The access opening 36 may be provided in the first layer 38 and have, but is not limited to, a shape that generally corresponds to the outer peripheral edge of the patch body. In this manner, the first layer may have, but is not limited to, an annular configuration. Alternative arrangements for forming the pocket are contemplated as should be apparent to one of skill in the art. For example, and without limitation, the pocket may be formed with a single layer of material in which the outer peripheral region of the layer is folded over the main portion of the material and secured to form the pocket between the main layer and the fold.

The first and second layers 38, 40 forming the pocket may be tissue infiltratable layers such as a mesh or other porous fabric amenable to tissue ingrowth to ensure tissue ingrowth across the entire first surface 24 of the patch body. In this manner, at least those portions of the second layer 26 exposed by the access opening 36, if not the entire second layer, would also be amenable to tissue ingrowth. If desired, a third layer (not shown) or coating may be provided over the surface of the second layer opposite the first layer as a barrier to adhesions between the first surface and sensitive organs or tissue. Alternative arrangements of a patch body are contemplated as should be apparent to one of skill in the art. For example, and without limitation, the patch body may include only tissue infiltratable layers, only solid or non-tissue infiltratable layers, or a combination of tissue infiltratable and non-tissue infiltratable aspects situated in the same layer. The patch body may also be configured without a pocket and/or access opening to a pocket.

A deployment device may be employed to position and provisionally hold the expanded patch against the abdominal wall pending fixation. The deployment device may be configured to be releasably coupled to the patch body. In one embodiment as shown in FIG. 1, the deployment device 50 may be placed within the pocket 34 of the patch body. However, other arrangements are contemplated for coupling the deployment device to the patch body, particularly for a patch body without a pocket. For example, and without limitation, the deployment device may include releasable fixating components for releasably connecting the deployment device to the patch body.

In one illustrative embodiment, the deployment device 50 may include a support body 52 that is removably insertable in the pocket 34 of the patch. A handle 54 may extend from the support body and through the access opening 36 when placed in the pocket. During a repair procedure, the handle 54 may be drawn through an opening, such as a surgical incision in the abdominal wall, to outside of the patient. A pulling force on the free end of the handle in an outward direction away from the support body 52 and the associated patch body 22 hoists the support body and patch body against the abdominal wall. The handle may also be used to maneuver the patch body into a desired positon relative to a hernia defect. As illustrated, the handle may extend from a central region of the support body. However, it is to be appreciated that the handle may extend from other regions of the support body suitable for manipulating, positioning and/or holding the patch against the abdominal wall, and thereafter separating the deployment device from the patch body.

The support body 52 may have a thin or reduced profile and, for example and without limitation, may be in the form of a flat sheet or sheets so as to minimize the overall thickness of the patch when assembled with the deployment device and reduced for delivery through the opening to the treatment site. The support body may be a continuous component or may include two or more discrete segments that are contiguous and/or spaced from each other which in combination form the support body.

The support body may have a size and shape that generally corresponds with the size and shape of the pocket. In an expanded configuration, the support body is larger than the access opening to the pocket and occupies a substantial portion of the pocket to facilitate maneuvering the patch body into position. In a collapsed or smaller configuration, the support body may be inserted into or removed from the pocket through the access opening.

To reduce movement between the deployment device and the patch body, the support body 52 may have an outer peripheral edge 56 that is located in close proximity to and generally follows the outer periphery 44 of the pocket when the support body is inserted and expanded in the pocket. The support body may be compliant to facilitate its collapsibility when inserted into and removed from the patch pocket, and when the assembled patch and deployment device are rolled up or otherwise reduced in shape for delivery to the treatment site.

Figure 4:
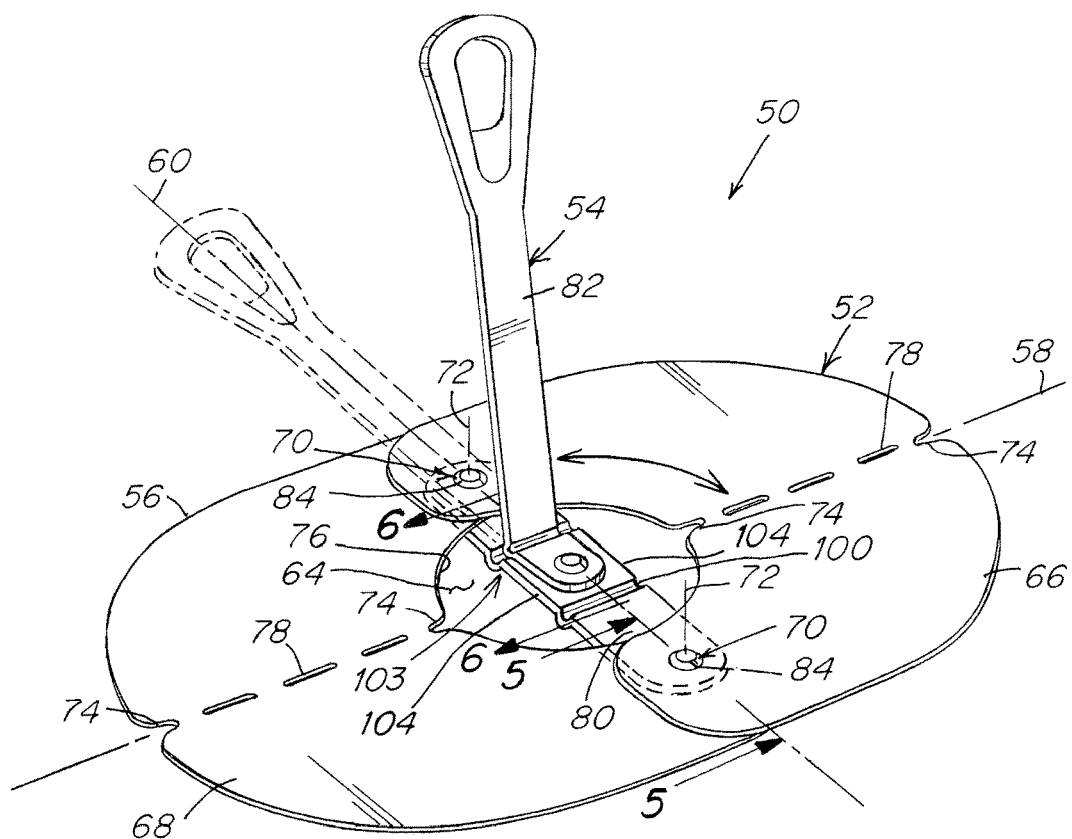
FIG. 4 is an illustration of an embodiment of a deployment device.
Figure 5:
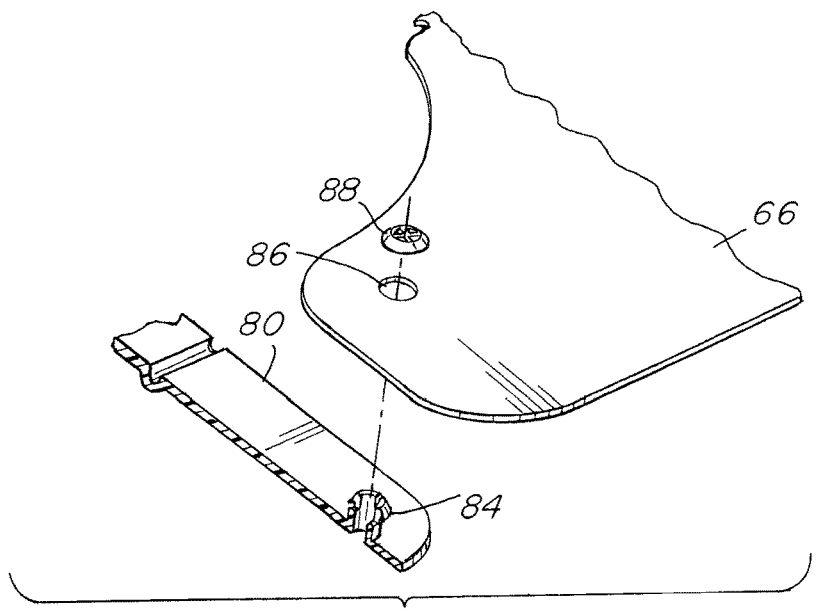
FIG. 5 is a sectional illustration of an arrangement for coupling the support segments of the deployment device taken along line 5-5 of FIG. 4.

In one illustrative embodiment, the support body 52 may have a planar configuration in the expanded configuration. As shown in FIG. 4, the support body may be defined by a first axis 58 and a second axis 60 that is substantially perpendicular to the first axis. The intersection of the first and second axes may coincide with a center 62, or approximate center, of the support body. An opening 64 may be located at the approximate center of the support body to facilitate its collapse to a smaller collapsed configuration for insertion into and withdrawal from the pocket of the patch.

In one illustrative embodiment shown in FIGS. 4-7, the support body 52 may include a first support segment 66 and a second support segment 68 movably coupled to each other to facilitate collapse of the support body to a non-planar configuration. In one embodiment, the first and second support segments may be coupled with a pair of hinges 70 which allow the segments to rotate relative to each other as the support body is collapsed for insertion into or withdrawal from the pocket and as the support body returns to the expanded configuration. The hinges 70 may be located along the second axis 60 on opposite sides of the first axis 58. As shown, portions of the support segments connected together may overlap each other and form an overlap region along the second axis. Each hinge 70 may be formed using a fastener, such as a rivet, screw, post or pin, or other suitable arrangement as should be apparent to one of skill in the art.

With the support body in the expanded, planar configuration, each hinge axis 72 extends in a direction perpendicular to a plane defined by the first and second axes 58, 60. To facilitate collapse of the support body, the first and second segments 66, 68 may be configured to bend, fold or flex about the first axis 58. This allows the positions of the hinges 70 to similarly move about the first axis as the support body is collapsed, thereby changing the orientation of the hinge axes 72 to extend in a direction more aligned with the second axis 60 to facilitate rotation of the segments relative to each other. In this manner, the hinges may move within a plane extending along the second axis 60 and perpendicular to the first axis 58 for rotation of the support segments.

Each support segment 58, 60 may include one or more features to facilitate bending, folding or flexing about the first axis. In one embodiment, each support segment may include a relief 74 located along the first axis 58 at the outer peripheral edge 56 of the support body and the inner peripheral edge 76 of the opening 64. The reliefs 74 may be configured to ease stress along the peripheral edges and promote bending, folding or flexing along the first axis. As shown, each relief may include a notch extending inwardly from the peripheral edge, although any suitable relief may be employed as should be apparent to one of skill.

For some applications, each support segment may include a preformed weakened region extending between the reliefs, or in lieu of reliefs, to promote bending, folding or flexing along the first axis. For example, the support segments may be formed from a material that, although sufficiently flexible for rolling the support body into a cylindrical shape, may nevertheless be difficult to bend, fold or flex about the first axis while pivoting the support segments about the hinges.

In one illustrative embodiment, the weakened region may include a series of spaced perforations 78 located along the first axis 58 that form a fold line for collapsing the support segments. For example, and without limitation, the perforations 78 may include circular holes, non-circular holes and/or elongated slots. However, the weakened region may employ any suitable arrangement that allows the support segment to bend, fold or flex about the first axis. For example, and without limitation, the weakened region may employ relatively weak or thin material as compared to adjacent material, and/or employ one or more score lines which permit bending, folding or flexing along the region.

In one embodiment, the handle 54 may include a handle base 80 that is attached to the support body and a handle pull 82 that extends from the handle base. The handle base 80 may be located along the second axis 60 and bridge across the first axis 58 and/or the opening 64 in the support body. As illustrated, the handle base may be located on a first side of the support body so that a pulling force on the handle pull in a direction extending away from the opposite second side of the support body is translated to the support body by the handle base in a direction toward the first side of the support body.

The handle base 80 may be configured to support and connect the support segments 66, 68 together. In one embodiment, the handle base may include a pair of fasteners 84 located on opposite sides of the first axis 58 and along the second axis 60. The fasteners may extend through holes 86 in the support segments to couple the segments together with the handle base. The fasteners 84 may be configured to form the hinges for the support segments. In one embodiment, the support segments may be mounted to fasteners, such as posts, protruding from opposite end portions of the handle base and secured with a collar 88 that snaps over a free end of each post. However, any fastening arrangement suitable for coupling the support segments to the handle base may be employed as should be apparent to one of skill in the art.

The handle pull 82 may be pivotal and/or rotatable relative to the handle base 80. A shown in FIGS. 4 and 7, the handle pull 82 may be arranged to pivot toward and away from the support body along the first axis 58 and/or the second axis 60 to facilitate collapsing the deployment device with the associated patch body and positioning the handle pull for manipulation and/or withdrawal of the support body from the patch body. For example, and without limitation, the handle pull may be positioned along the first axis 58 and pivoted toward and in close proximity to the support body to allow the deployment device and associated patch to be rolled into a reduced cylindrical shape along the first axis for delivery to the treatment site through the surgical opening. After deployment, the handle pull may be pulled away from the support body and through the surgical opening with the handle pull positioned along the first axis. Alternatively, the handle pull may be arranged along the second axis 60, or in any desired position between the first and second axes. If desired, the handle pull 82 may be rotatably mounted to the handle base 80 to permit rotation of the handle pull to any suitable position relative to the first and second axes. For example, the handle pull may be repositioned along the second axis 60, or repositioned in any desired position between the first and second axes.

Figure 6A:
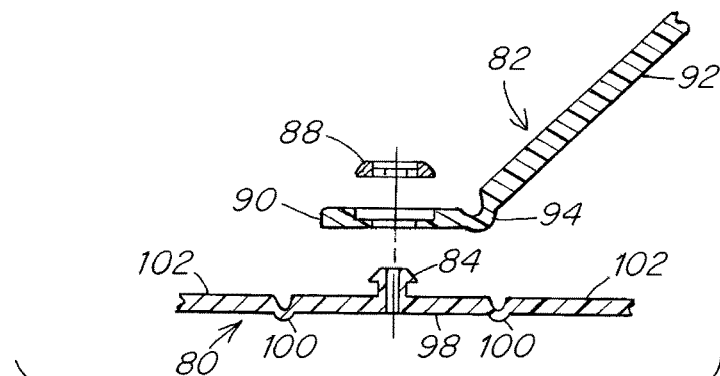
FIG. 6A is an exploded sectional view of an arrangement for mounting the handle of the deployment device taken along line 6-6 of FIG. 4.
Figure 6B:
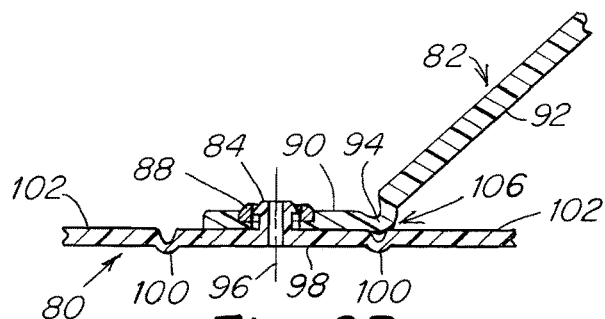
FIG. 6B is an assembled sectional view of the arrangement for mounting the handle of the deployment device taken along line 6-6 of FIG. 4.
Figure 7:
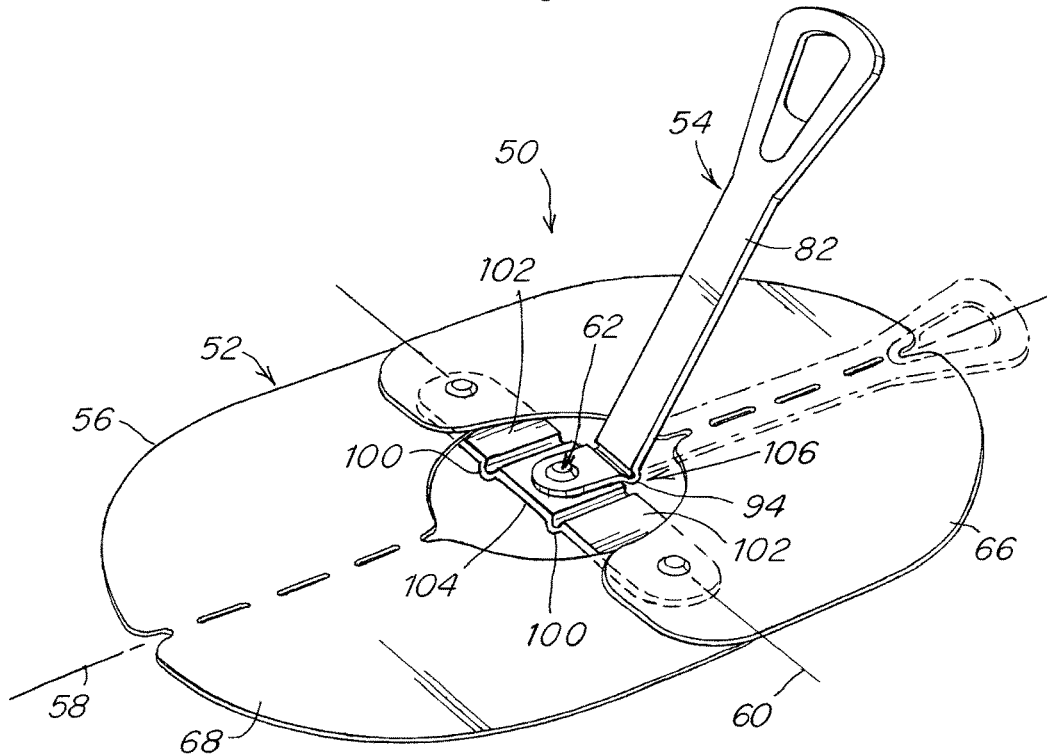
FIG. 7 is an illustration of a deployment device similar to FIG. 5 with the handle repositioned along the first axis.

As shown in FIGS. 4 and 6A-6B, the handle pull 82 may have an elongated configuration with a mount component 90 for mounting the handle pull to the handle base and a grip component 92 extending from the mount component for manipulating the support body and associated patch body. The grip component 92 may be pivotally coupled to the mount component 90 to allow the grip component to pivot toward and away from the support body. In one embodiment, the handle pull 82 may include a hinge 94 which couples the grip component to the mount component. In one embodiment, the hinge may be a living hinge integrally formed with the handle pull, although other arrangements for coupling the grip component to the mount component may be employed as should be apparent to one of skill in the art.

As indicated above, the handle pull 82 may be rotatably mounted to the handle base 80 so that the handle pull may be positioned along the first axis 58 and the second axis 60, as well as positions between the first and second axes, if desired. In one embodiment, the mount component 90 may be rotatably mounted to a central portion of the handle base 80 about a third axis 96 located at the approximate center of the support body and perpendicular to the first and second axes. Similar to the support segments, the mount component may be mounted to a fastener 84, such as a post, protruding from a central portion 98 of the handle base and secured with a collar 88 that snaps over a free end of the post. However, any fastening arrangement suitable for rotatably mounting the handle pull to the handle base may be employed as should be apparent to one of skill in the art.

For some applications, the handle base 80 may be sufficiently stiff to manipulate the support body and associated patch body in the extended configuration at the treatment site, as well as translate a pulling force from the handle pull 82 to collapse and withdraw the support body from the patch and treatment site. To ensure adequate collapsibility of the deployment device for insertion into and withdrawal from the patch body and treatment site, the handle base 80 may be configured to bend, fold and/or flex at one or more predetermined regions. For example, the handle base may be provided with one or more weakened regions of reduced stiffness. In one embodiment shown in FIGS. 6A-6B, the handle base 80 may include a pair of hinges 100 which couple the central portion 98 to the end portions 102 at opposite sides of the central portion. Each hinge 100 may be oriented in a direction parallel to the first axis 58 to facilitate rolling, folding, bending and flexing of the deployment device about the first axis. Each hinge 100 may be a living hinge integrally formed with the handle base, although other arrangements may be employed as should be apparent to one of skill in the art.

For some applications, it may be desirable retain the handle pull 82 in one or more selected positions. For example, and without limitation, the handle may be configured to retain the handle pull 82 in positions along the first axis 58, the second axis 60 and/or positions between the first and second axes. In one embodiment shown in FIGS. 6A-6B, the handle may include a detent 103 between the handle pull 82 and the handle base 80 that is configured to hold the handle pull in position when rotated to extend along the first axis and/or the second axis. In one embodiment, the detent may include the hinge 94 of the handle pull 82 being configured to coact with a side edge 104 of the handle base to retain the handle pull in a first position along the first axis, and to coact with a hinge 100 of the handle base to retain the handle pull in a second position along the second axis. Other arrangements suitable for retaining the handle pull in a selected position may also be employed as should be apparent to one of skill in the art.

Figure 8A:
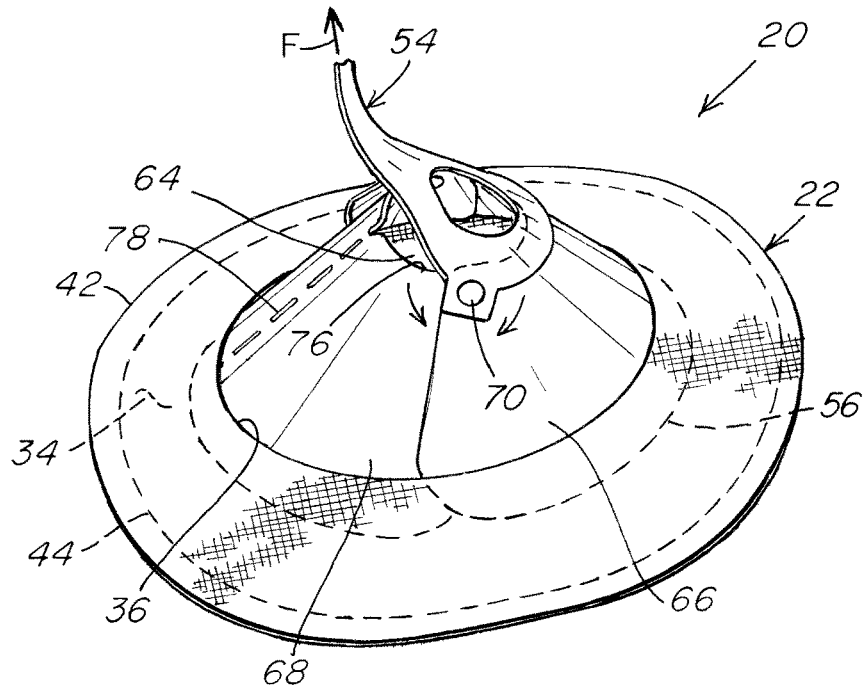
FIGS. 8A-8C are illustrations of the prosthesis of FIG. 1 with the deployment device in various stages of collapse to a non-planar configuration for insertion into or withdrawal from the pocket of the hernia repair patch.
Figure 8B:
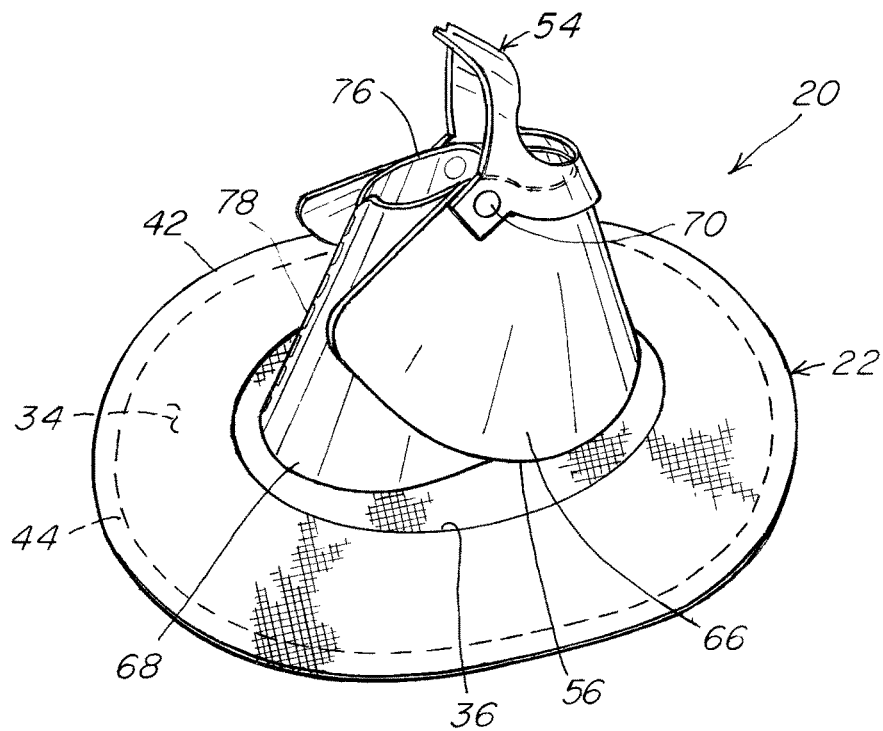
Figure 8C:
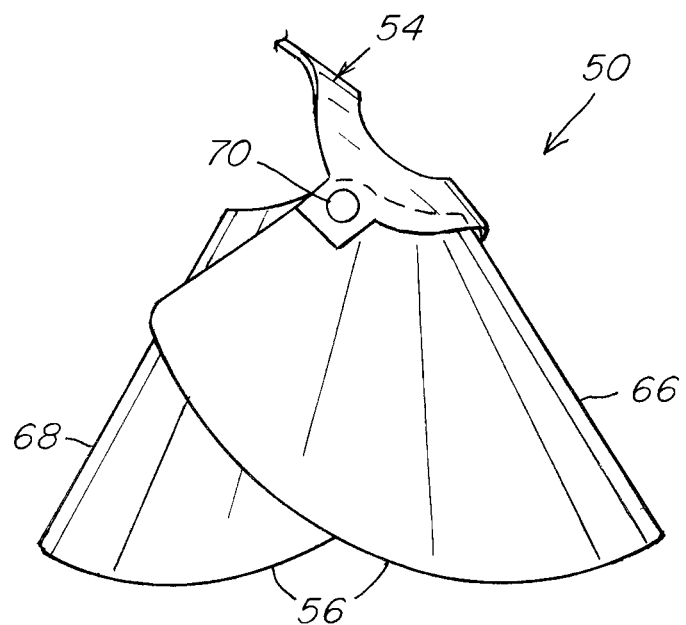
Figure 9:
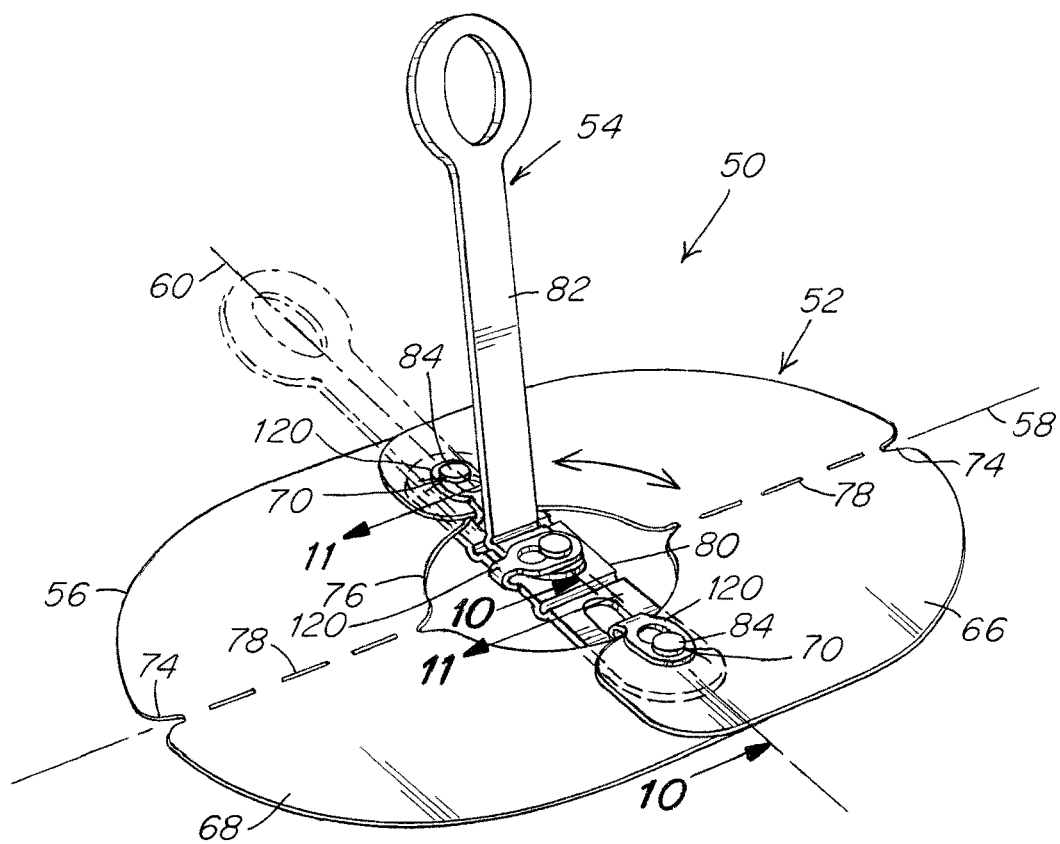
FIG. 9 is an illustration of another embodiment of a deployment device.

As illustrated in FIGS. 8A-8B, a pulling force F on the handle 54 encourages the support segments 66, 68 to rotate about the hinges 70 and fold about the first axis to collapse the support body into a collapsed configuration having a reduced size relative to the access opening to permit withdrawal of the support body from the pocket of the patch body. In one illustrative embodiment, the support segments rotate toward each other with the second support segment 68 folding and rotating within the first support segment which similarly folds and rotates over the second support segment. In this manner, portions of the first and second support segments overlap each other in the collapsed configuration, for example, in a petal-like arrangement. As illustrated in FIG. 8C, the support segments may be configured to collapse the support body into a generally flattened, non-planar configuration having a generally trapezoidal shape. In this regard, the inner peripheral edge 76 of the opening and the outer peripheral edge 56 of the support body generally define the bases of the trapezoidal shape and the fold lines of the support segments extending along the first axis 58 generally define the nonparallel legs of the trapezoidal shape. Such an arrangement may reduce the pulling force required to remove the deployment device from the pocket of the patch body with minimal, if any, spraying of bodily fluids resulting from withdrawal of the deployment device from the surgical site.

FIGS. 9-32 illustrate additional embodiments of a deployment device 50 to position and provisionally hold an expanded patch against the abdominal wall pending fixation. Each deployment device 50 may include a support body 52 formed with first and second support segments 66, 68 coupled together and may implement one or more of the features to facilitate collapse of the support body, as described above. Each deployment device may employ a different handle arrangement, as described below.

In an illustrative embodiment shown in FIGS. 9-12, the support segments 66, 68 and the handle pull 82 may be coupled to the handle base 80 using keyhole fastening arrangements. The handle base 80 may include a fastener 84, such as a post, at the central portion for mounting the handle pull and a fastening post 84 at each end portion for coupling the support segments.

The support segments 66, 68 may include a keyhole opening 110 that cooperates with each post 84 on the end portions 102 of the handle base 80 to couple the support segments to the base. Each post 84 includes an enlarged head 112 that is sized to pass through the enlarged end 114 of the keyhole but not pass through the small end 116 of the keyhole. As shown, the keyholes 110 in the support segments are arranged to extend along the second axis 60 with the enlarged end of the keyhole located closer toward the outer periphery of the support body. The keyholes 110 may be positioned so that flexing the support segments about the first axis 58 reduces the spacing between the keyholes to allow passage of each post 84 through the large end 114 of the corresponding keyhole. As the flex in the support segments is released, the spacing between the keyholes increases thereby positioning each post 84 in the small end 116 of its corresponding keyhole.

Figure 10:
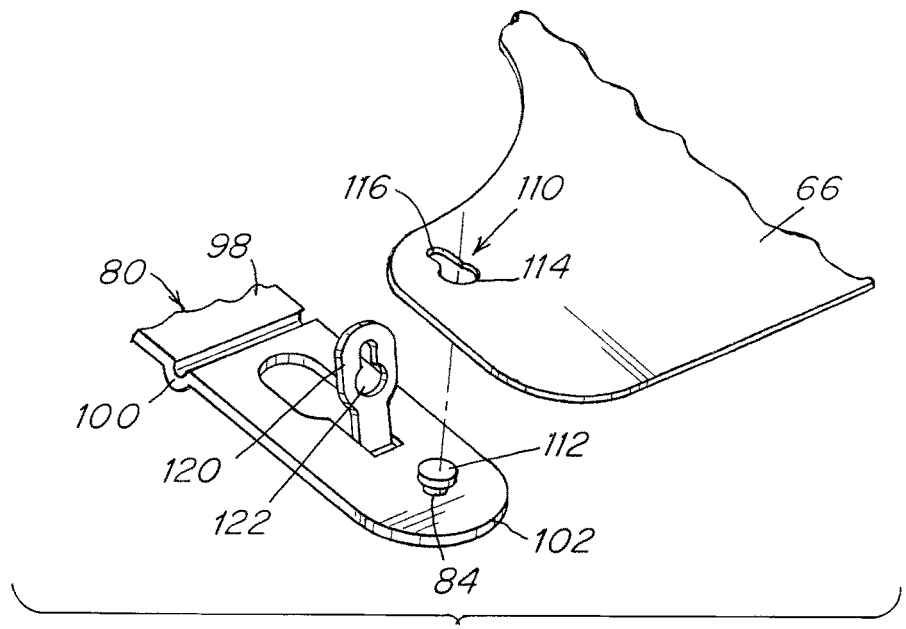
FIG. 10 is a sectional illustration of an arrangement for coupling the support segments of the deployment device taken along line 10-10 of FIG. 9.

The handle base 80 may include tabs 120 with a keyhole opening 122 that cooperates with the posts 84 to secure the support segments to the handle base. As shown in FIG. 10, the keyholes 122 in the tabs are arranged to extend along the second axis 60 with the enlarged end of the keyhole located closer toward the central portion of the support body. In this manner, the tab keyholes 122 employ an orientation opposite to the keyholes 110 in the support segments and work together to secure the support segments to the handle base during collapse and expansion of the support body. As shown, the tabs 120 may be flexibly coupled to the end portions 102 of the handle base.

Figure 11A:
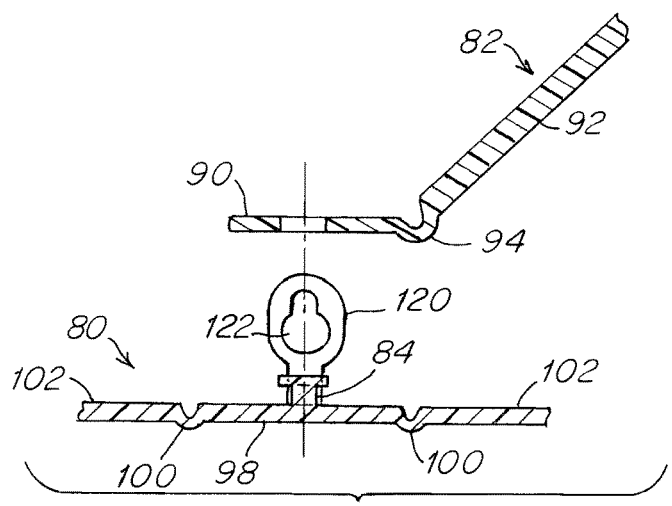
FIG. 11A is an exploded sectional view of an arrangement for mounting the handle of the deployment device taken along line 11-11 of FIG. 9.
Figure 11B:
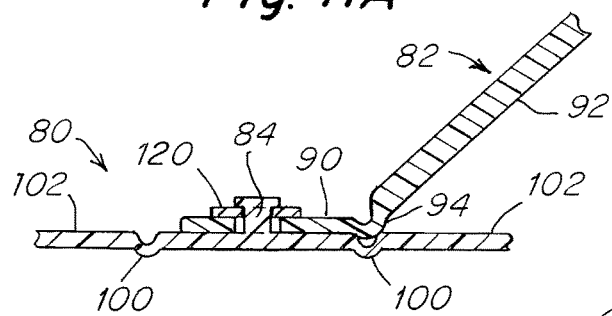
FIG. 11B is an assembled sectional view of the arrangement for mounting the handle of the deployment device taken along line 11-11 of FIG. 9.
Figure 12:
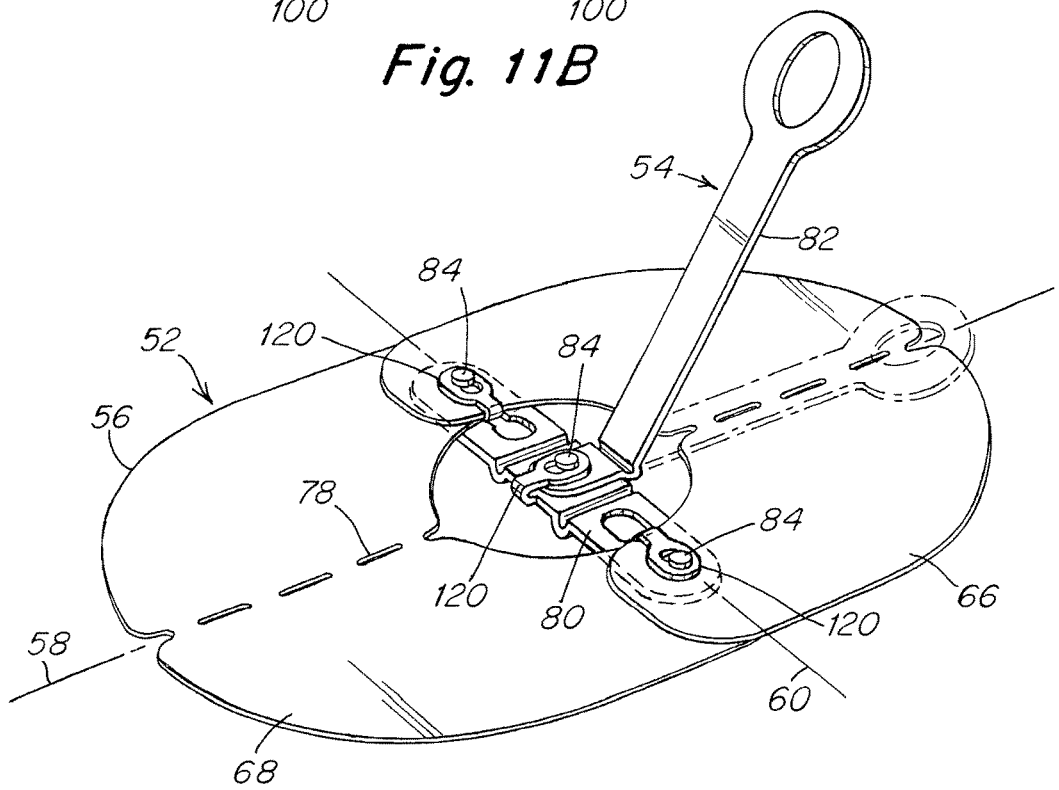
FIG. 12 is an illustration of a deployment device similar to FIG. 9 with the handle repositioned along the first axis.
Figure 13:
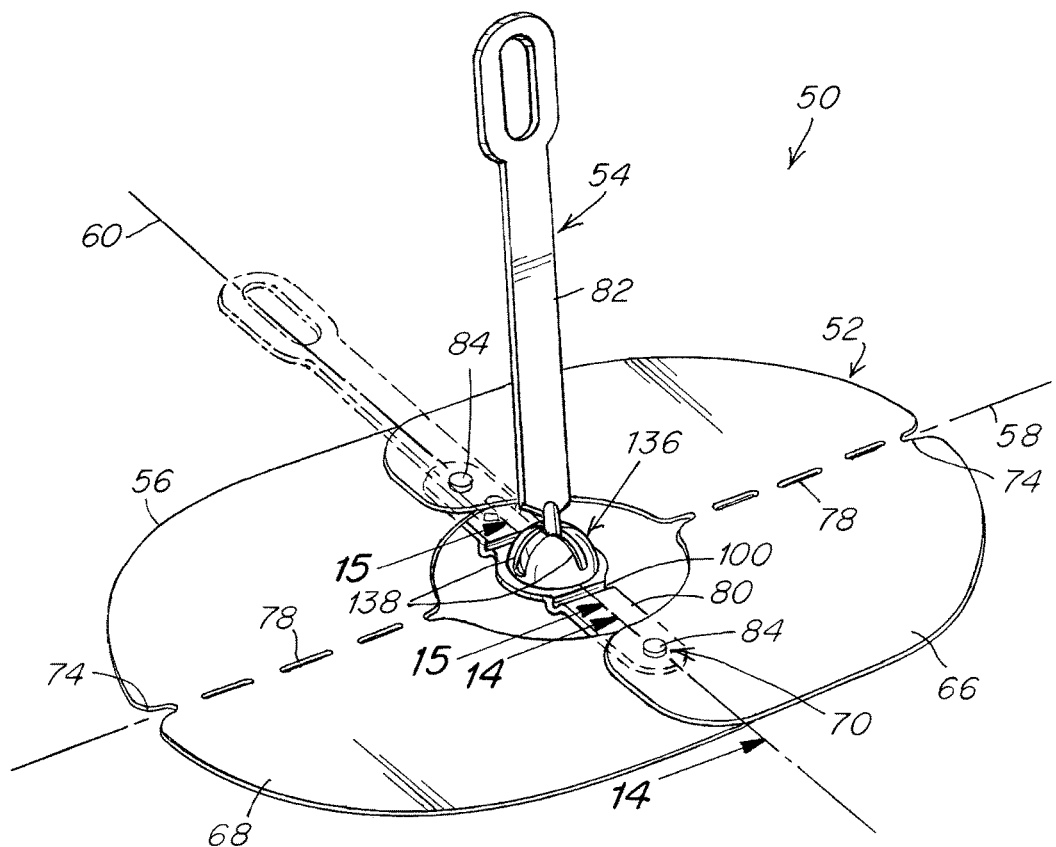
FIG. 13 is an illustration of another embodiment of a deployment device.

The handle pull 82 may be mounted to the center portion of the handle base 80 in a similar manner. As shown in FIGS. 11A-11B, the mount component 90 of the handle pull may include an opening 124 that receives the post 84 extending from the central portion 98 of the handle base. A tab 120 with a keyhole opening 122 extends from the side edge 104 of the central portion to lock the mount component on the post. The handle pull may be rotated about the post to position it along the first or second axes, as desired.

Figure 14:
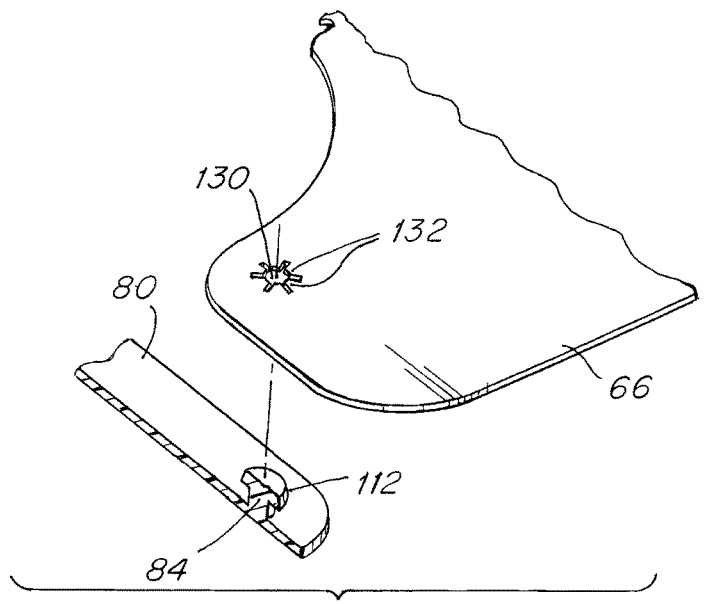
FIG. 14 is a sectional illustration of an arrangement for coupling the support segments of the deployment device taken along line 14-14 of FIG. 13.

In an illustrative embodiment shown in FIGS. 13-16, the support segments may be coupled to the handle base using a snap-fit fastening arrangement. The handle base 80 may include a post 84 at each end portion 102 for coupling the support segments. The support segments may include an opening 130 configured to snap onto each post on the end portions of the handle base to couple the support segments to the base. As shown in FIG. 14, each post includes an enlarged head 112 that is sized to be pressed through the corresponding opening 130 in the support segment. As shown, the openings 130 in the support segments may employ a fan finger arrangement in which inwardly extending fingers 132 around the opening are configured to flex over the enlarged head 112 of the post and then return to their initial non-flexed state below the post head to secure the support segments to the handle base.

Figure 15A:
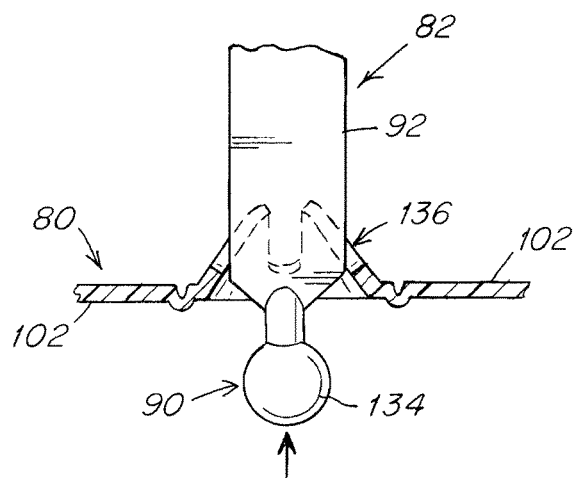
FIG. 15A is an exploded sectional view of an arrangement for mounting the handle of the deployment device taken along line 15-15 of FIG. 13.
Figure 15B:
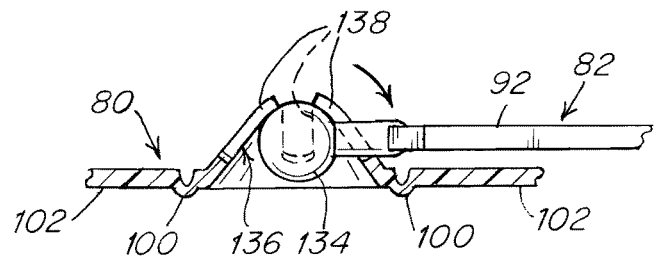
FIG. 15B is an assembled sectional view of the arrangement for mounting the handle of the deployment device taken along line 15-15 of FIG. 13.
Figure 16:
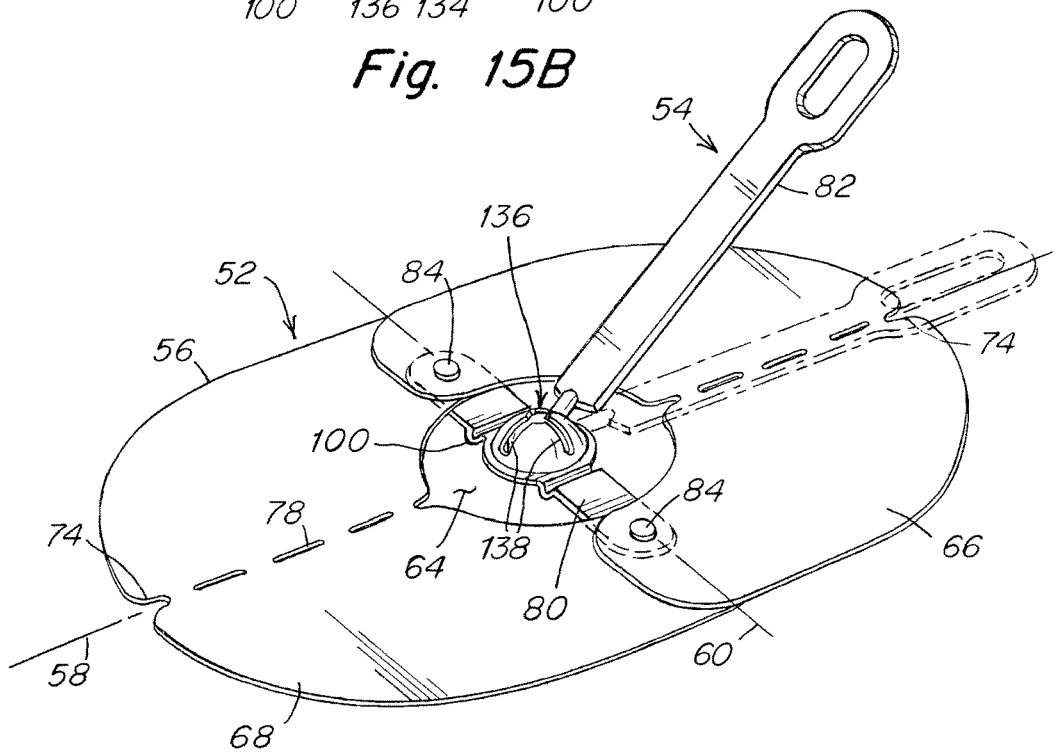
FIG. 16 is an illustration of a deployment device similar to FIG. 13 with the handle repositioned along the first axis.
Figure 17:
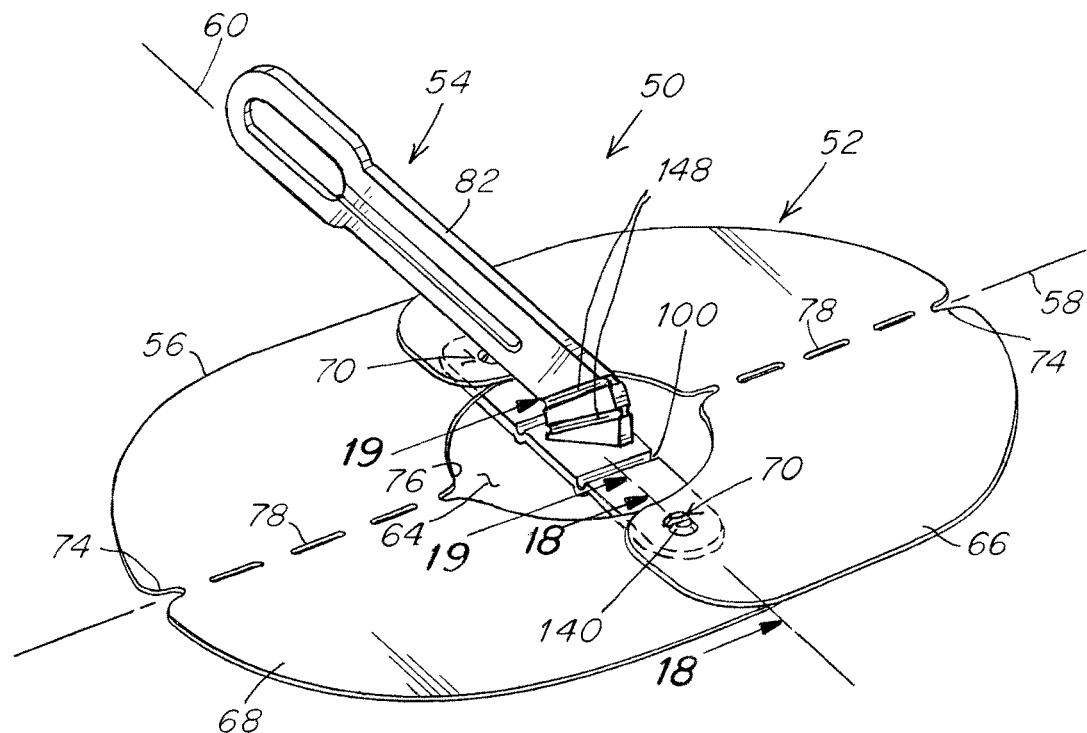
FIG. 17 is an illustration of an embodiment of a deployment device.

The handle pull 82 may be pivotally mounted to the handle base 80 using a ball and socket arrangement. In one embodiment, the mount component 90 of the handle pull may be configured as a ball 134 and the central portion of the handle base 80 may include a socket 136 configured to receive the ball of the mount component. As shown in FIGS. 15A-15B, the handle pull 82 may be assembled to the handle base 80 by inserting the grip component 92 through the socket 136 so that the ball 134 is received in and held by the socket. The socket 136 may include one or more slots 138 configured to allow passage of the grip component through the socket while capturing the ball of the mount component therein. In one embodiment, the socket 136 may include slots 138 along the first axis 58 and the second axis 60 of the deployment device to allow the handle pull to be pivoted along these axes.

Figure 18:
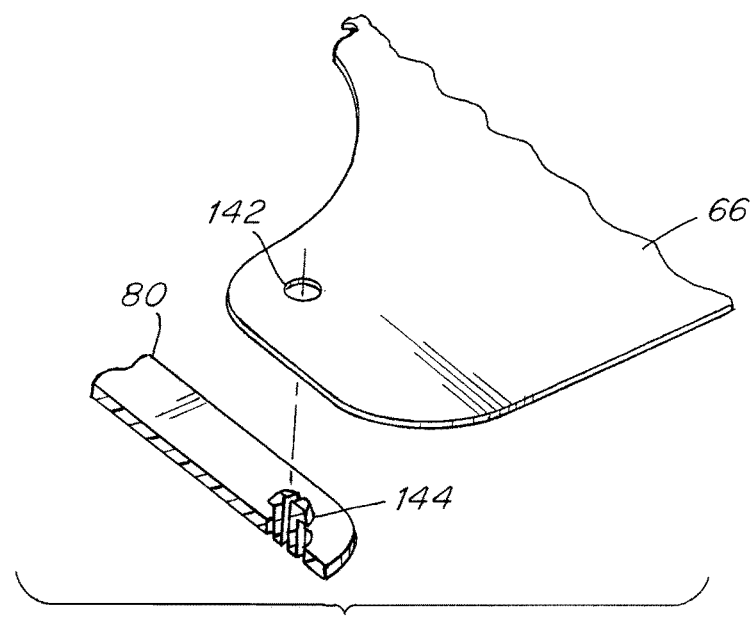
FIG. 18 is a sectional illustration of an arrangement for coupling the support segments of the deployment device taken along line 18-18 of FIG. 17.

In an illustrative embodiment shown in FIGS. 17-21, the support segments 66, 68 may be coupled to the handle base 80 using a snap-fit fastening arrangement. The handle base may include a fastener 140, such as a post, at each end portion for coupling the support segments. As shown in FIG. 18, the support segments may include an opening 142 configured to snap onto each post on the end portions of the handle base to couple the support segments to the base. Each fastening post 140 may employ a resilient post arrangement with an enlarged head 144 that is sized to be pressed through the corresponding opening in the support segment. As shown, each post 140 may include a pair of spaced resilient fingers 146 configured to flex toward each other to pass through the openings as the support segments are pressed onto the post. After passage through the openings, the fingers 146 spring back to their initial non-flexed state so that the post head 144 secures the support segments to the handle base.

Figure 19:
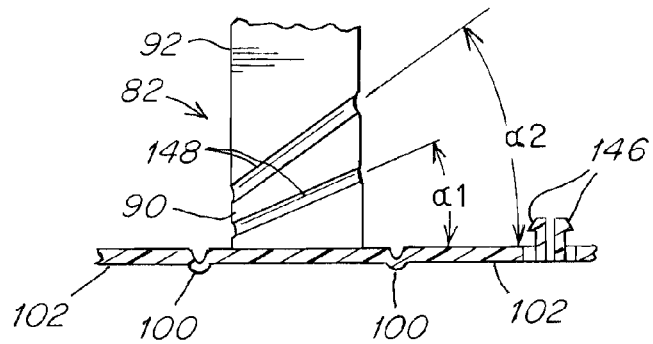
FIG. 19 is a sectional illustration of a hinged handle arrangement taken along line 19-19 of FIG. 17.
Figure 20:
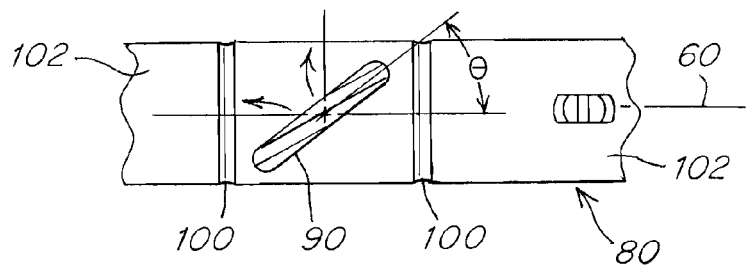
FIG. 20 is a partial top view of the handle arrangement of FIG. 19.
Figure 21:
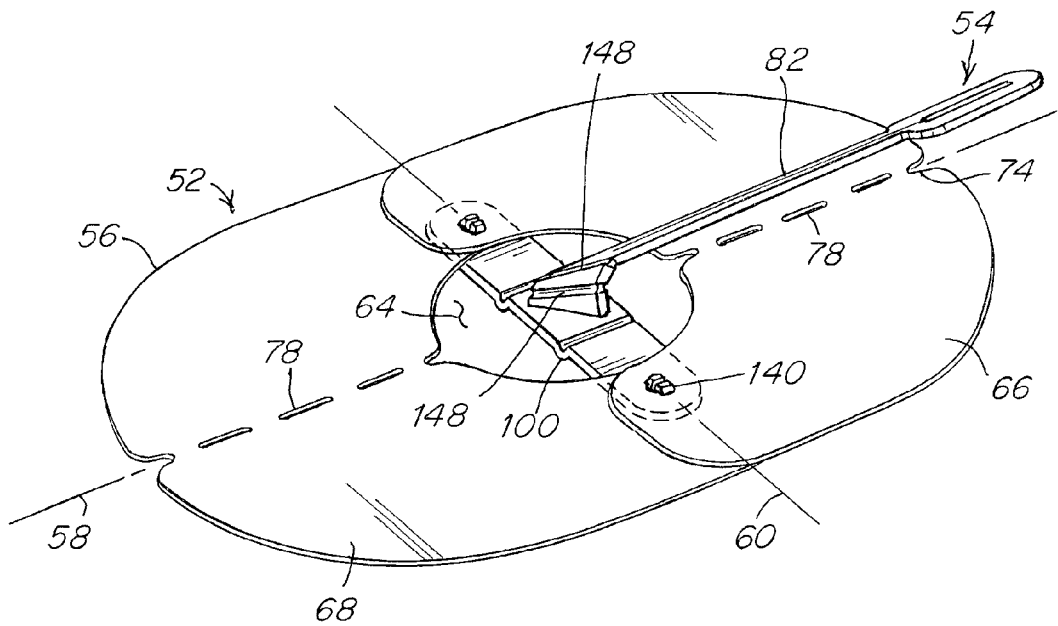
FIG. 21 is an illustration of a deployment device similar to FIG. 17 with the handle repositioned along the first axis.
Figure 22:
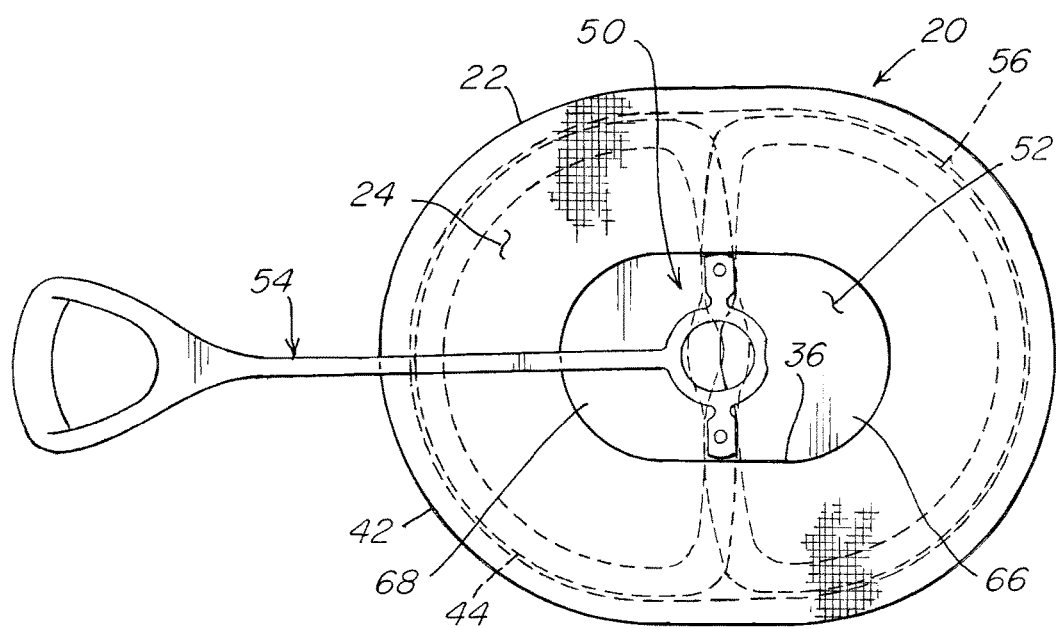
FIG. 22 is another illustration of a prosthesis for repairing a hernia defect with an assembled hernia repair patch and deployment device in an expanded configuration.

The handle pull 82 may be pivotally mounted to the handle base 80 using a flexible hinge arrangement. In one embodiment, the mount component 90 of the handle pull may be configured to permit the grip component 92 to be pivoted, for example, by folding, to extend along the first and second axes. As shown in FIGS. 19-20, the mount component may include, but is not limited to, a pair of hinges 148 having different angular orientations $\alpha_1$, $\alpha_2$ relative to each other with the mount component 90 having an angular orientation $\Theta$ relative to the first and second axes 58, 60 conducive to folding the grip component along each axis.

In one embodiment, the handle 54 may employ a unitary structure with the handle pull 82 integrally formed with the handle base 80. The hinges 148 may include living hinges integrally formed with the mount component. The mount component 90 may be oriented at an angle $\Theta$ of approximately 45 degrees to the first and second axes, and the hinges 148 may be oriented at angles $\alpha_1$ of approximately 23 degrees and $\alpha_2$ of approximately 35 degrees relative to the plane defined by the first and second axes 58, 60. Other hinge arrangements are contemplated as should be apparent to one of skill in the art.

In illustrative embodiments shown in FIGS. 22-32, the handle pull 82 may be integrally formed with the handle base 80 as a single structure. The handle base may include a pair of mounting segments 83 located on opposite sides of the first axis 58 and along the second axis 60. Fasteners 84 may extend through holes 86 (FIG. 26) in the support segments to couple the support segments together with the handle base. The fasteners 84 may be configured to form the hinges for the support segments. In one embodiment, the support segments may be coupled to the handle base with individual fasteners that extend through holes (not shown) in the mounting segments of the handle base and secured with a collar 88 (FIG. 25) that snaps over a free end of each fastener.

The handle base 80 may include a pair of connector segments 99 which couple a central portion 98 of the base to the mounting segments 83 at opposite sides of the central portion. Each connector segment 99 may be oriented in a direction along the second axis 60 and be sufficiently flexible to facilitate rolling, folding, bending and flexing of the deployment device about the first axis. Each connector segment 99 may be integrally formed with the handle base, although other arrangements may be employed as should be apparent to one of skill in the art.

As indicated above, the support segments 66, 68 may be configured to roll, bend, fold or flex to facilitate collapse of the support body for insertion into and withdrawal from the pocket of the patch, as well as rolling of the patch and support body for delivery to a surgical site. The support segments may also have a sufficient amount of resilience to return to an expanded or open configuration to expand and support the patch after delivery for placement at the surgical site.

In one embodiment, each support segment 66, 68 may include a resilient support member to help deploy the support body, and thereby the patch, into an expanded configuration, such as a planar configuration. As illustrated in FIGS. 23-28, the resilient support member 101 may include a continuous loop or ring that extends along the outer margin of the support segment. As shown, the support member 101 may be positioned at the outer peripheral edge 56 of the support segment. However, the support member may be spaced inwardly from the outer peripheral edge and/or at discrete locations throughout the body of the support segment as should be apparent to one of skill in the art.

As illustrated, each support member 101 may have an annular configuration of a desired width and thickness to provide a desired degree of resilience or rigidity. Each support member may have a generally D-shape configuration that corresponds to the shape of the support segments. Each support member may include a curved outer portion 103 and a center portion 105 that connects the ends of the outer portion. As shown, the center portion 105 may have an undulating configuration that facilitates collapse and expansion of the support body. However, the support member may have any suitable shape and/or cross section as should be apparent to one of skill in the art.

Rather than using a separate support member, it may be desirable to construct each support segment from a single sheet of material that alone provides the desired amount of flexibility, foldability, rollability, resiliency and support. Such an arrangement may reduce costs associated with fabricating the support segments.

Figure 29:
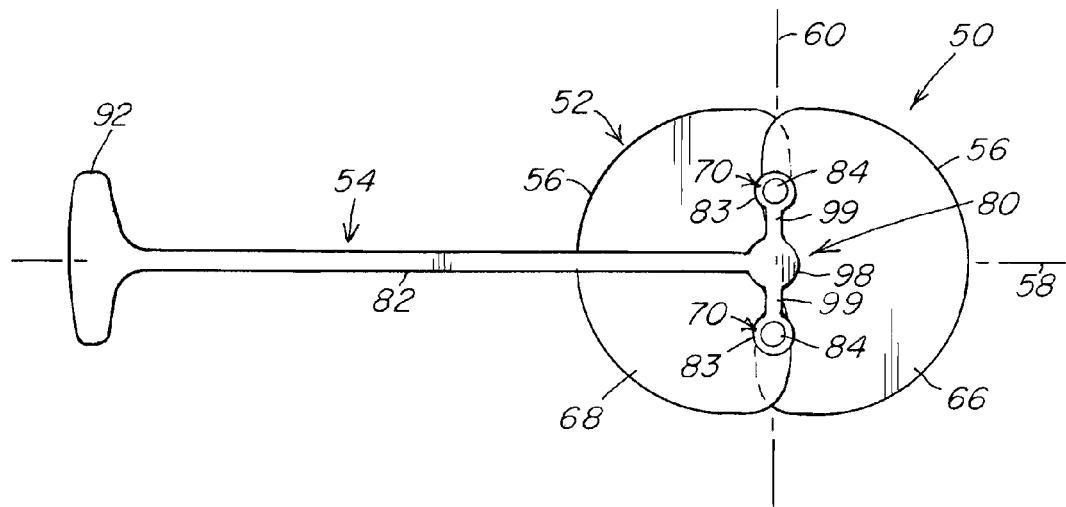
FIGS. 29-31 are illustrations of another embodiment of a deployment device with alternating overlap of the support segments.
Figure 30:
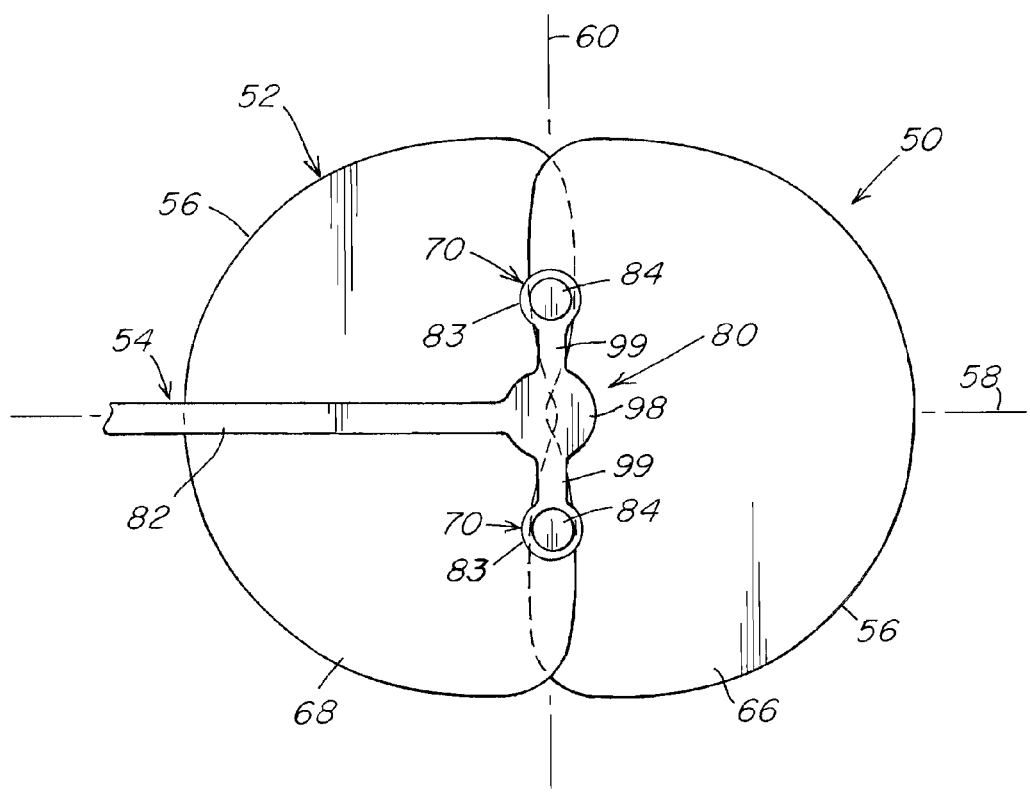
Figure 31:
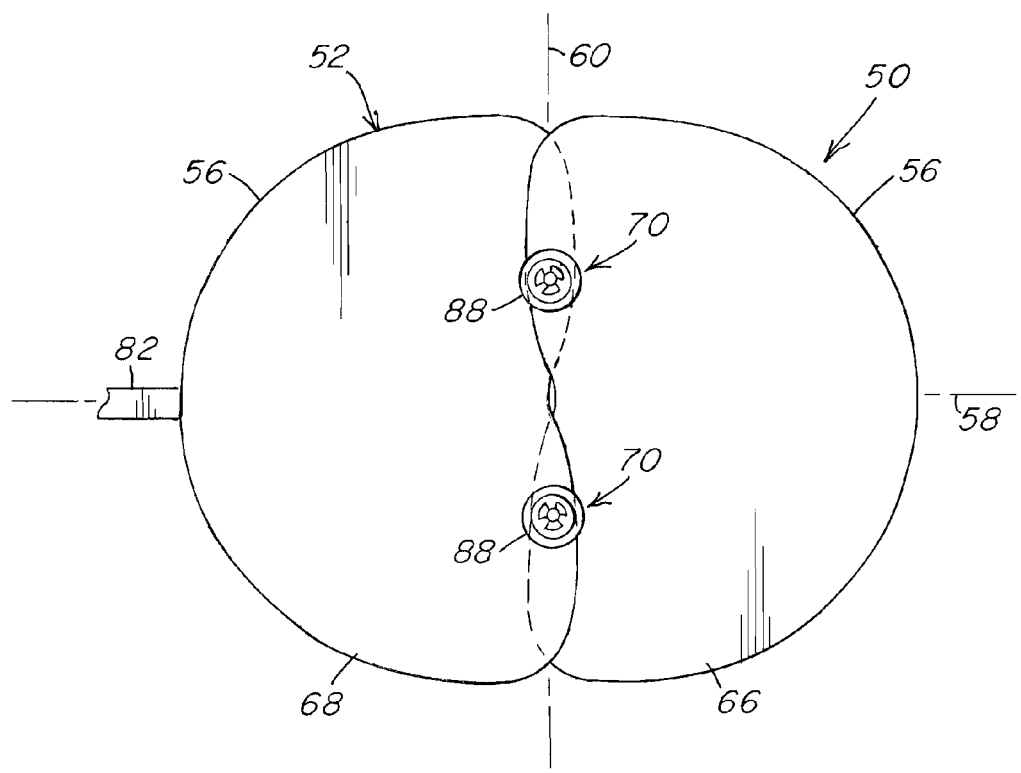

As shown in FIGS. 29-31, each support segment 66, 68 may be formed from a sheet of material that alone provides a desired balance of flexibility, stiffness and resilience for allowing the support body to be collapsed and expanded while providing support for the patch. For example and without limitation, each support segment may be fabricated from a sheet of plastic material that provides the support body with the desired support properties, as well as other properties including, but not limited to, strength and/or stress crack resistance.

Figure 23:
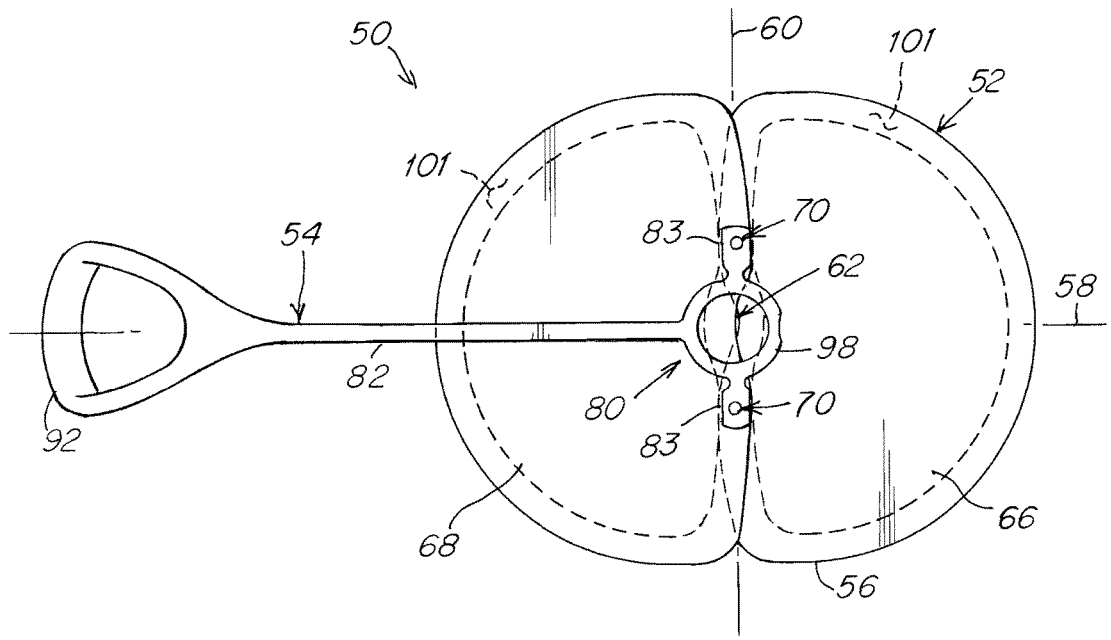
FIG. 23 is an illustration of another embodiment of a deployment device.
Figure 24:
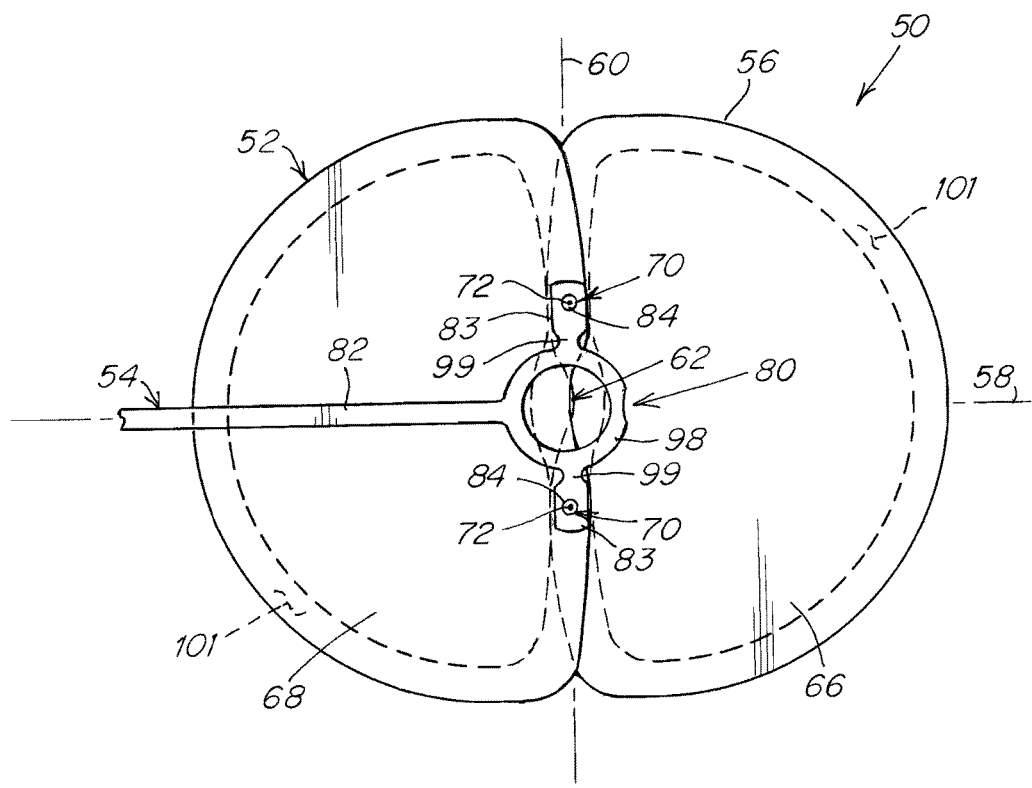
FIG. 24 is an enlarged top view of the support body of the deployment device of FIG. 23.
Figure 25:
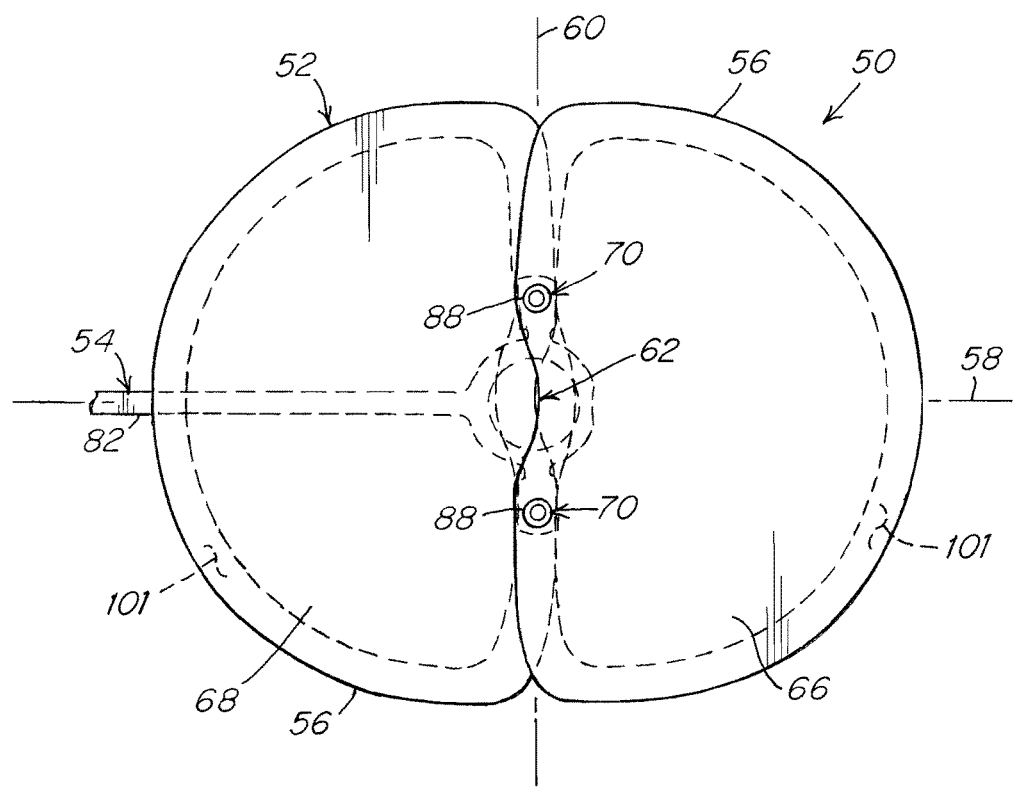
FIG. 25 is a bottom view of the support body of the deployment device of FIGS. 23-24.
Figure 26:
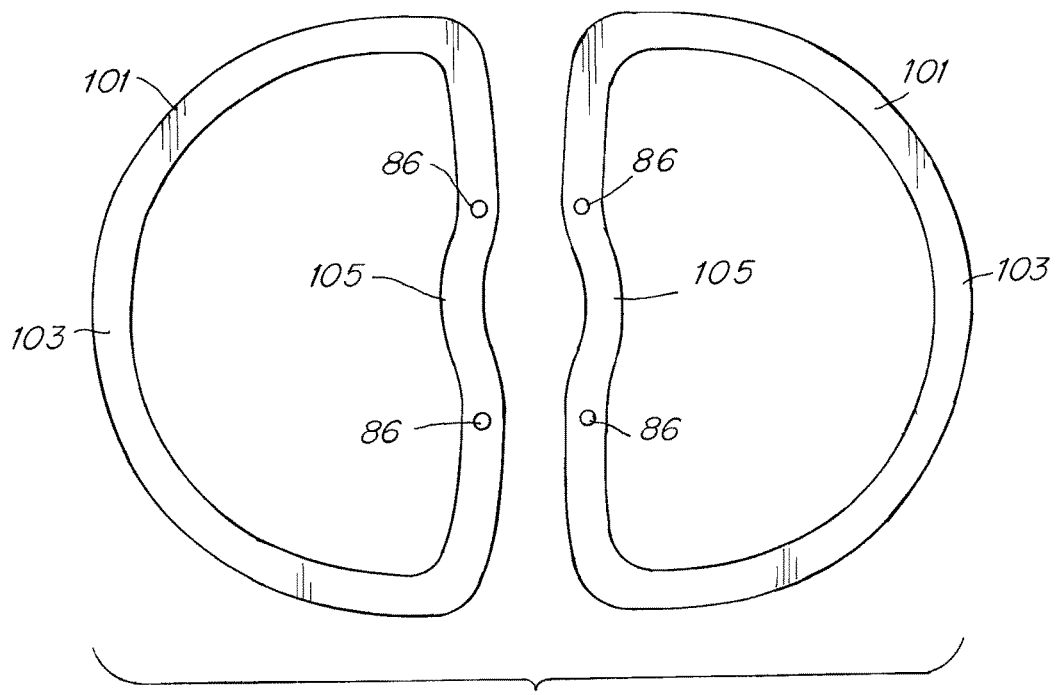
FIG. 26 is an illustration of an embodiment of support members for the support segments of the deployment device of FIGS. 23-25.
Figure 27:
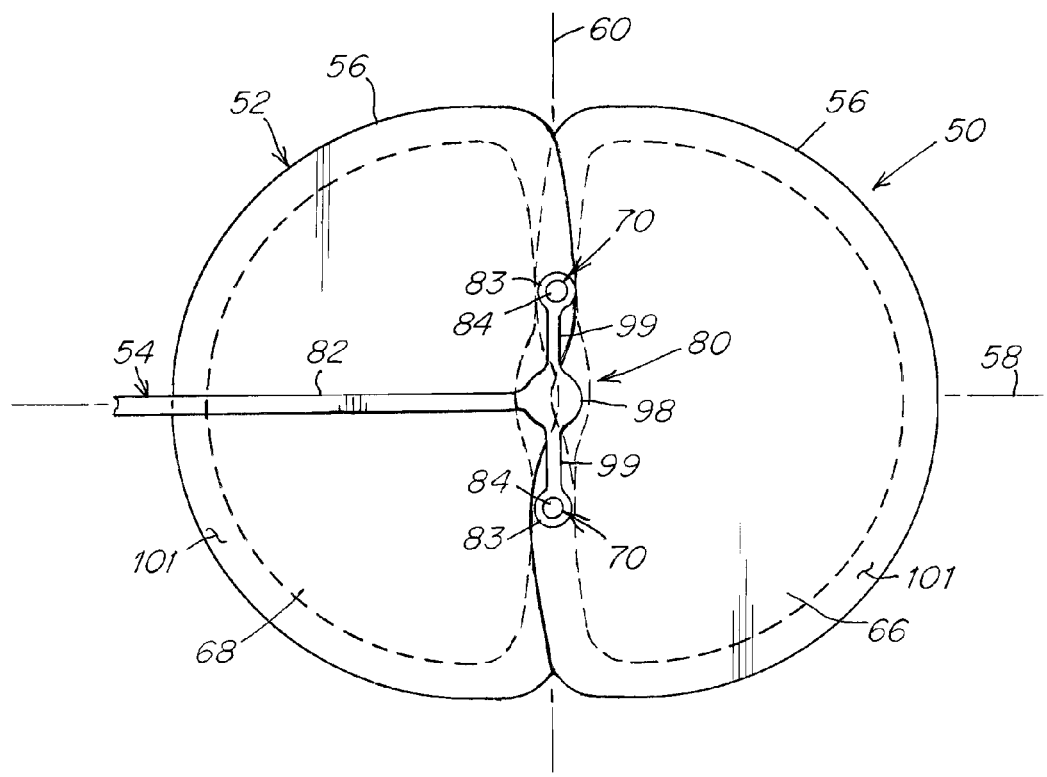
FIGS. 27-28 are illustrations of another embodiment of a deployment device with alternating overlap of the support segments.
Figure 28:
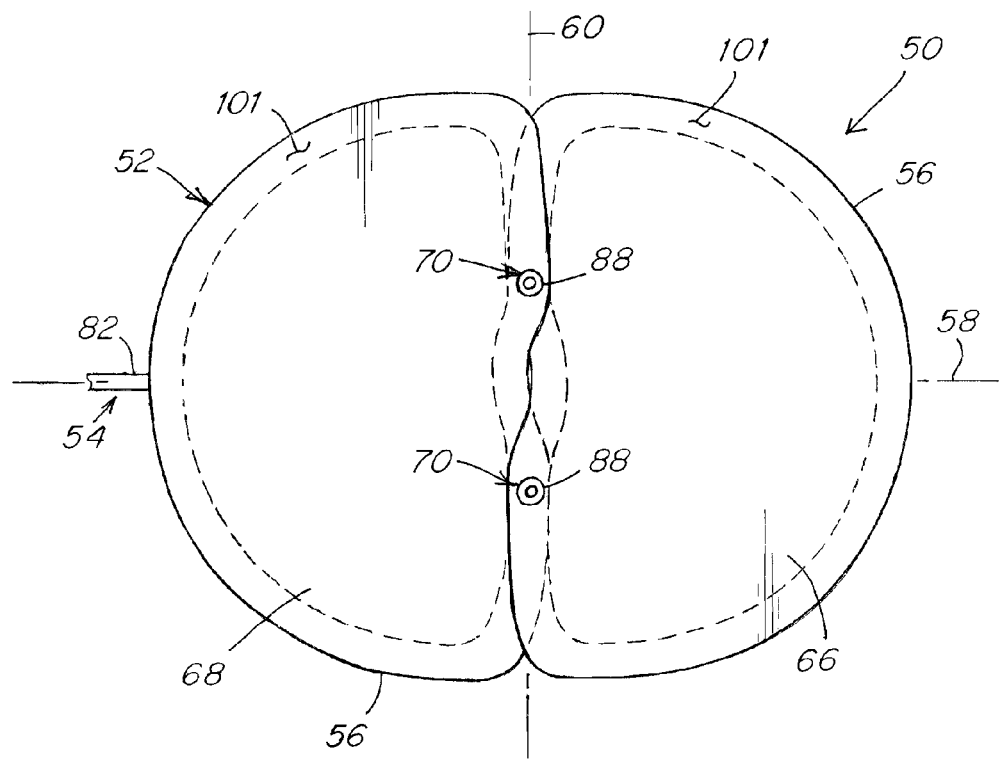

As described above, portions of the support segments 66, 68 connected together may overlap each other and form an overlap region along the second axis 60. In one embodiment as shown in FIGS. 23-25, the first support segment 66 may overlap the same side of the second support member 68 along the entire length of the overlap region. In another embodiment as shown in FIGS. 27-31, the overlap between the first and second support segments may alternate along the length of the overlap region. As shown, the first support segment may overlap one side of the second support segment along a portion of the overlap region above the first axis and may overlap the opposite side of the second support segment along a portion of the overlap region below the first axis. An alternating overlap arrangement between the first and second support segments may provide less contact or obstruction between the support segments when collapsed for withdrawal from the patch and/or may reduce the profile of the collapsed support body. It is to be appreciated that any suitable overlap arrangement, if desired, may be used between the support segments as should be apparent to one of skill in the art.

Figure 32:
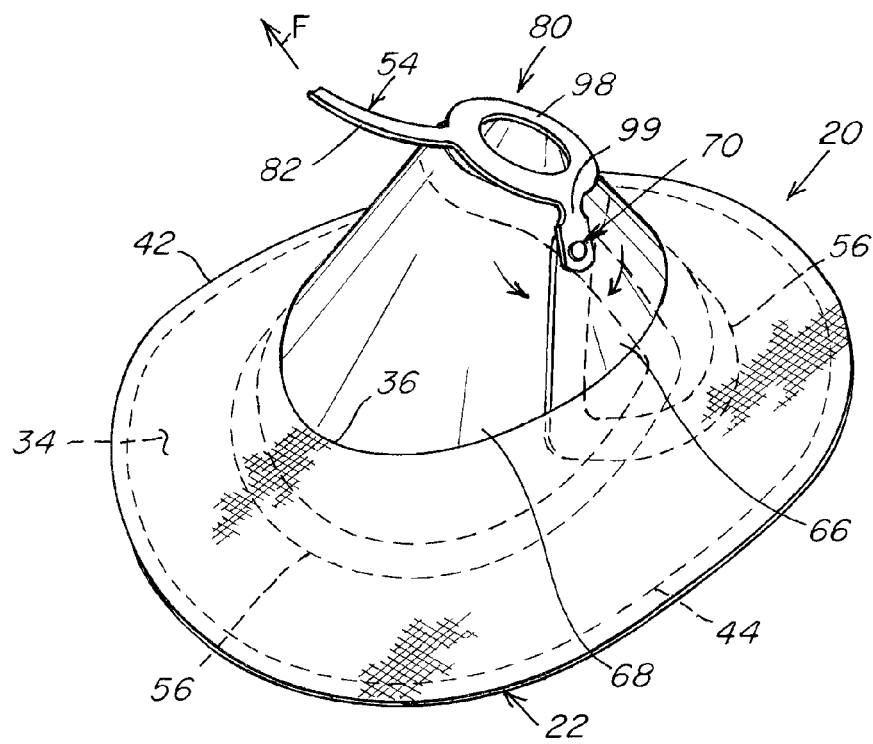
FIG. 32 is an illustration of the prosthesis of FIG. 22 with the deployment device in a stage of collapse to a reduced configuration for insertion into or withdrawal from the pocket of the hernia repair patch.
Figure 33:
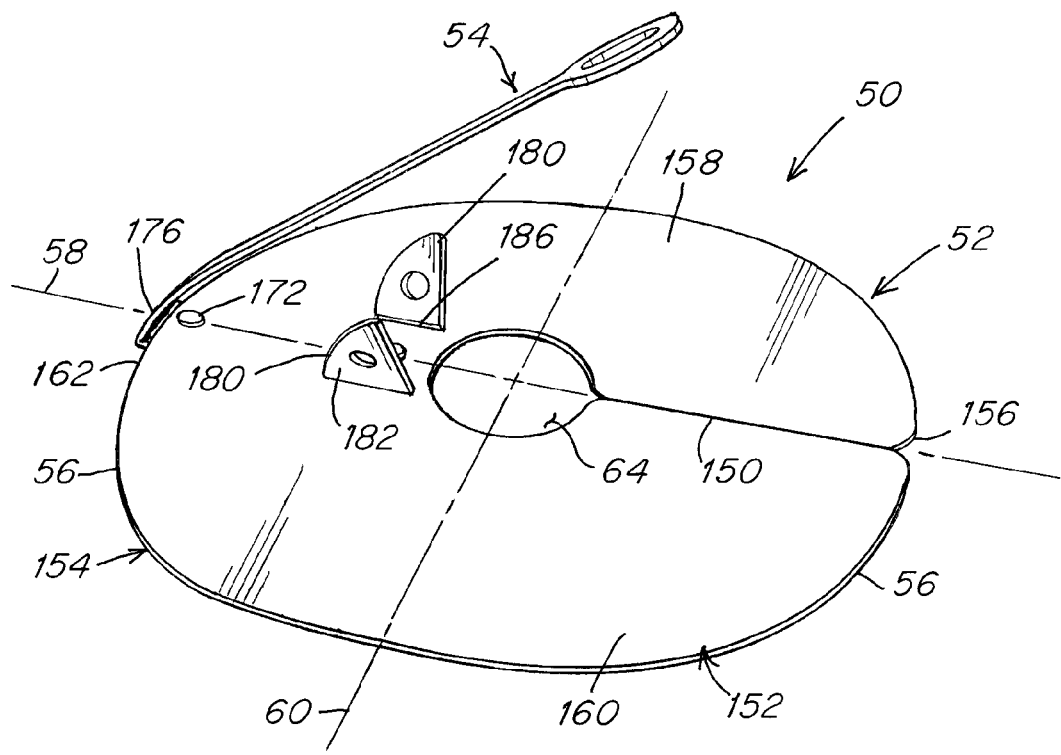
FIG. 33 is an illustration of a deployment device according to another embodiment.

As illustrated in FIG. 32, a pulling force F on the handle 54 encourages the support segments 66, 68 to rotate about the hinges 70 and fold about the first axis to collapse the support body into a collapsed configuration having a reduced size relative to the access opening to permit withdrawal of the support body from the pocket of the patch body.

In an illustrative embodiment associated with the deployment device of FIGS. 23-25, the support segments 66, 68 rotate toward each other with the second support segment 68 folding and rotating within the first support segment 66 which similarly folds and rotates over the second support segment.

In an illustrative embodiment associated with the deployment devices of FIGS. 27-31, the support segments 66, 68 rotate toward each other with a first portion of the second support segment 68 folding and rotating within a first portion of the first support segment 66 which similarly folds and rotates over the first portion of the second support segment, and with a second portion of the first support segment 66 folding and rotating within a second portion of the second support segment 68 which similarly folds and rotates over the second portion of the first support segment.

In each arrangement, portions of the first and second support segments overlap each other in the collapsed configuration, for example, in a petal-like arrangement. However, it is to be appreciated that the support segments may be configured to collapse in any suitable arrangement as should be apparent to one of skill in the art.

As illustrated in FIG. 32, the support segments 66, 68 may be configured to collapse the support body into a generally conical or frusto-conical configuration. As described above, the support segments may be configured to collapse the support body into a generally flattened, non-planar configuration having a generally trapezoidal shape. In this regard, the inner peripheral edge of the support segments and the outer peripheral edge 56 of the support body generally define the bases of the trapezoidal shape and the fold or bend lines of the support segments extending along the first axis 58 generally define the nonparallel legs of the trapezoidal shape. Such arrangements may reduce the pulling force required to remove the deployment device from the pocket of the patch body with minimal, if any, spraying of bodily fluids resulting from withdrawal of the deployment device from the surgical site.

In alternate embodiments illustrated in FIGS. 33-49, the deployment device 50 may include a support body 52 employing a single piece structure for insertion into the pocket of the prosthesis. The support body 52 may include a first portion 152 and a second portion 154 on opposite sides of the second axis 60.

A handle 54 may be coupled to the second portion 154 and arranged to direct a pulling force to the outer peripheral edge 56 at a second end 162 of the support body opposite the first end 156 along the first axis 58. In one embodiment, the handle 54 may extend from a location outside the outer peripheral edge at the second end of the support body. As shown, the handle may be arranged to extend along the first axis.

In one embodiment illustrated in FIGS. 33-36, an opening 64 may extend through the support body to facilitate collapse of the support body for insertion into and removal from the pocket. A radial slit 150 may extend from the opening to the outer peripheral edge 56 of the support body. As shown, the opening 64 may be located at the approximate center of the support body. The slit 150 may be located on the first portion 152 of the support body and extend along the first axis 58 from the opening to a first end 156 of the support body. The first portion may include first and second segments 158, 160 on opposite sides of the first axis 58. Edges of the first and second segments defining the slit may substantially abut along the length of the slit to provide a substantially continuous planar surface across the first and second segments. It is to be appreciated that the size and/or location of the opening and/or slit may be chosen to provide the support body with a desired collapsibility as should be apparent to one of skill in the art. It is also to be appreciated that the an opening and/or slit are not necessary and may be omitted from the support body.

Figure 36:
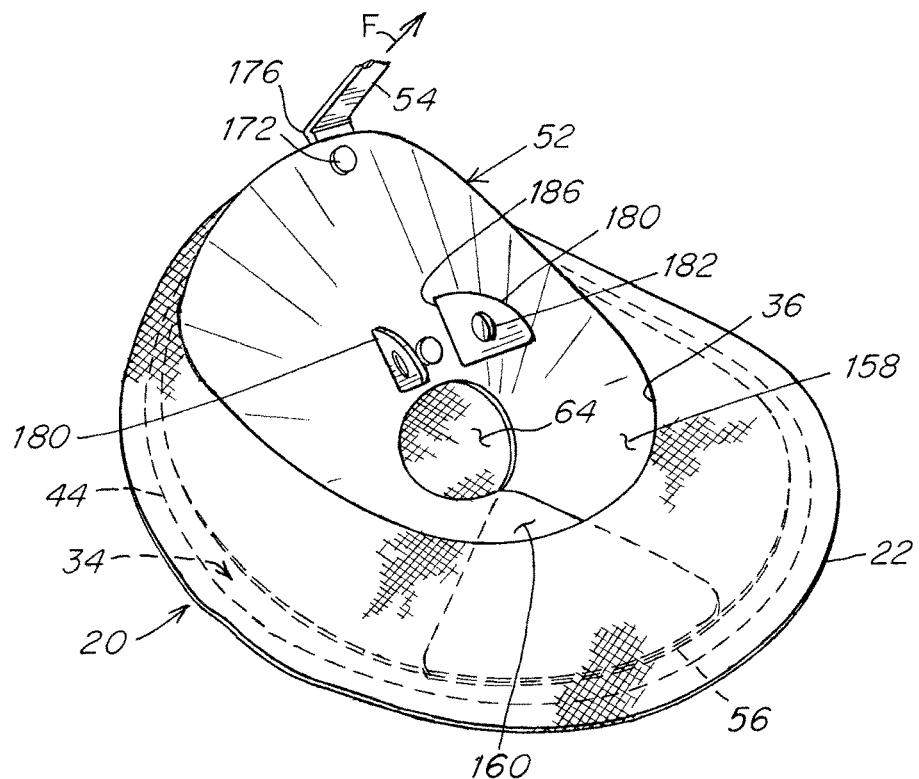
FIG. 36 is an illustration of the prosthesis of FIG. 35 with the deployment device collapsed to a reduced configuration for withdrawal from the pocket of the hernia repair patch.

Applying a pulling force F on the handle, as illustrated in FIG. 36, encourages the support body to pivot and fold into a reduced configuration, such as non-planar configuration, with portions of the first and second segments 158, 160 of the support body overlapping each other. As illustrated, pulling the handle in an outward direction away from the patch body draws the second end 162 of the support body away from the patch body. Directing the pulling force toward the outer peripheral edge at the second end of the support body causes at least a segment of the second portion to lift and pivot about a region generally parallel to the second axis 60 while also folding about the first axis 58 as the support body is withdrawn through the access opening of the pocket. Such an arrangement may reduce the pulling force required to remove the deployment device from the pocket of the patch body with minimal, if any, spraying of bodily fluids resulting from the deployment device being withdrawn from the surgical site.

Figure 34:
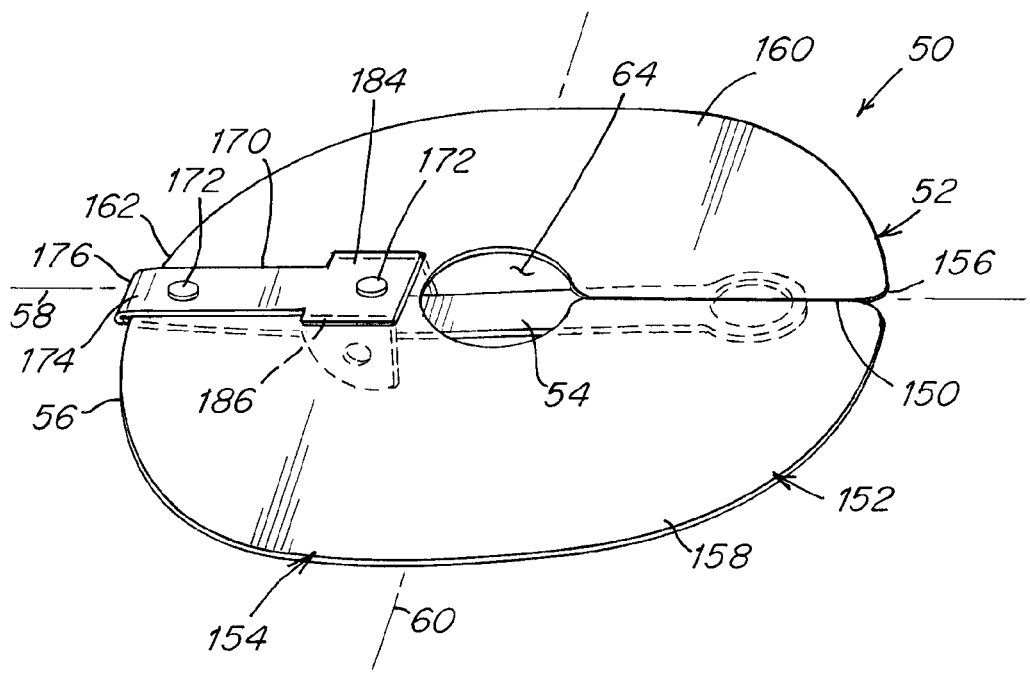
FIG. 34 is a bottom view of the deployment device of FIG. 33.
Figure 35:
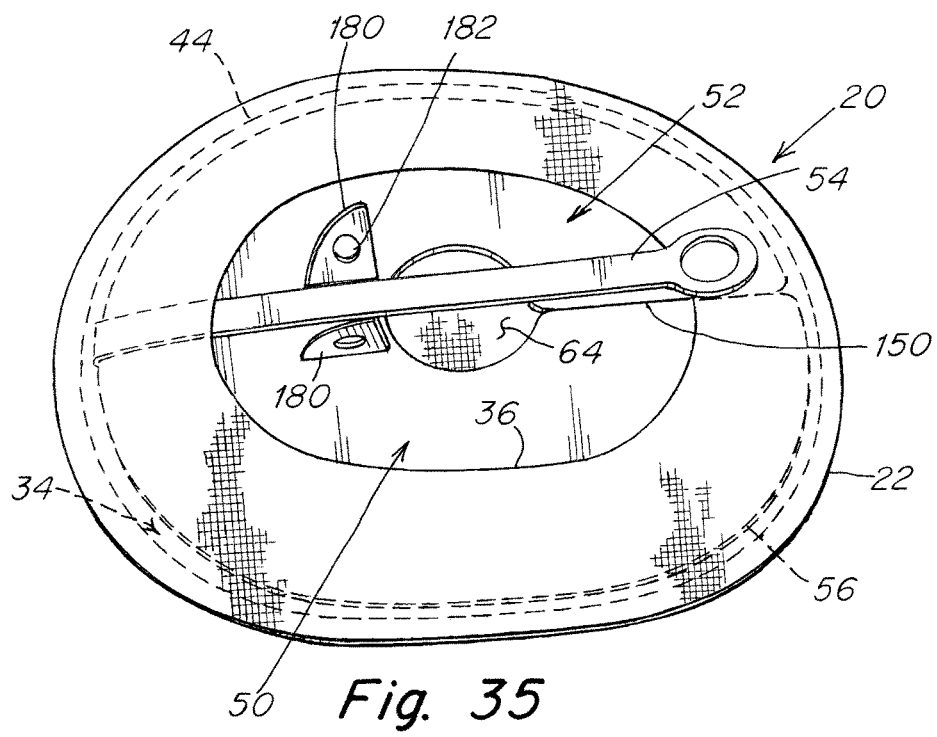
FIG. 35 is an illustration of a prosthesis for repairing a hernia defect with an assembled hernia repair patch of FIG. 2 and deployment device of FIG. 33 in an expanded configuration.

A force translation component may be provided to translate the pulling force across a region of the support body from the outer peripheral edge at the second end toward the opening. As shown in FIG. 34, the force translation component 170 may be located along the first axis 58 adjacent a first side of the support body opposite the handle 54 so that a pulling force on the handle is applied in an outward direction away from an opposite second side of the support body and against the first side of the support body. The force translation component 170 may have an elongated configuration extending from a location proximate the opening 64 to a location adjacent the peripheral edge 56. The force translation component may be attached to the support body using fasteners 172, including as rivets or screws, or otherwise secured, such as by welding or bonding with an adhesive, as should be apparent to one of skill in the art.

The handle 54 may extend from an end 174 of the force translation component 170 extending beyond the outer peripheral edge 56 at the second end 162 of the support body. The handle 54 and the force translation component 170 may be integrally formed as a single structure with an integral hinge 176, such as a living hinge, or other pivoting feature coupling the handle to the force translation component. Alternatively, the handle and force translation component may be separately fabricated components coupled together with a separate hinge or otherwise fastened to each other using any suitable arrangement as should be apparent to one of skill in the art.

An arrangement having the handle extending from a location adjacent the outer peripheral edge of the support body may potentially render positioning and/or manipulation of the support body with the handle difficult, if not ineffective. To facilitate positioning the patch body relative to the hernia defect, the deployment device may include one or more grips 180 extendable away from the support body.

Each grip 180 may have a size and/or configuration conducive for being grasped and manipulated by hand and/or surgical tool. Each grip may include one or more features configured to enhance a surgeon's ability to grasp and manipulate the deployment device and associated patch body into position at the treatment site. As shown, each grip 180 may include a hole 182 extending therethrough to enhance the ability to grasp the grip. Additionally or alternatively, other grip features may be employed as should be apparent to one of skill in the art.

Each grip 180 may be movable relative to the support body to facilitate manipulation of the patch body and the support body into the reduced configuration for insertion through a surgical opening into a patient. For example, and without limitation, each grip may be foldable, pivotal or flexible relative to the support body.

Each grip may 180 be located on the second portion 154 between the opening 64 and the second end 162 of the support body. As shown, a pair of grips 180 may be located on opposite sides of the first axis 58. In one embodiment, the grips may be coupled to an end 184 of the force translation component opposite the handle and extend through the support body. The grips and the force translation component may be integrally formed as a single structure with an integral hinge 186, such as a living hinge, or other pivoting feature coupling the grips to the force translation component. Alternatively, the grips and force translation component may be separately fabricated components coupled together with a separate hinge or otherwise fastened to each other using any suitable arrangement as should be apparent to one of skill in the art.

Figure 37:
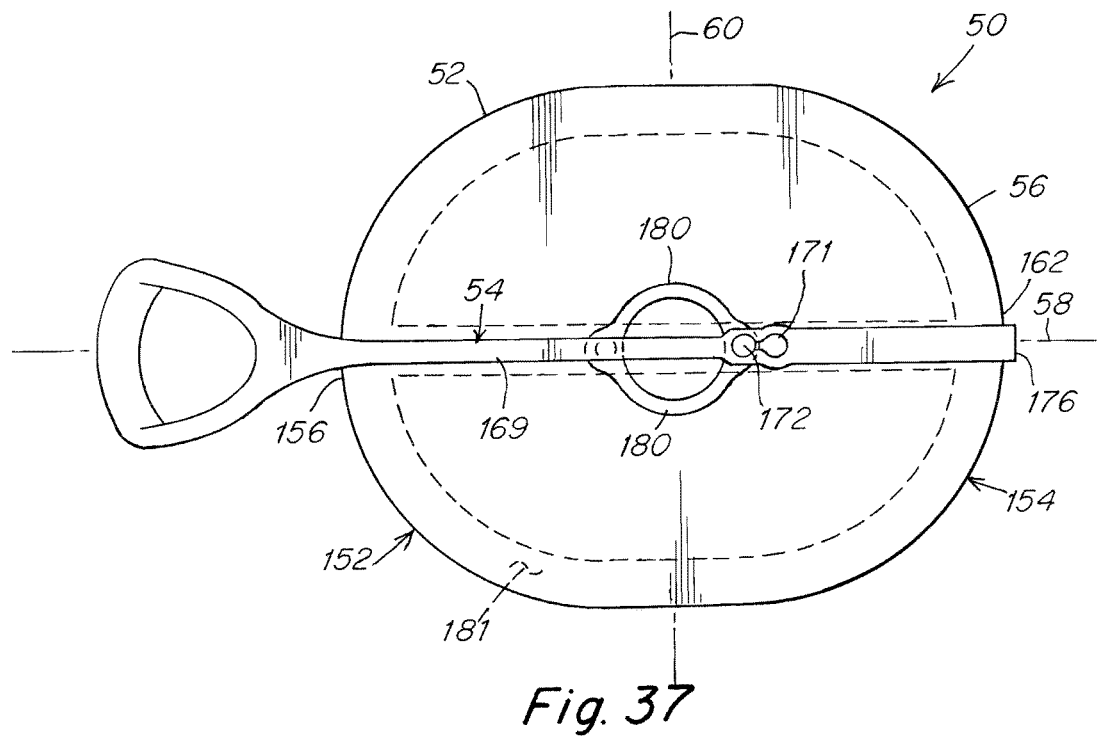
FIG. 37 is a top view of another embodiment of a deployment device.
Figure 38:
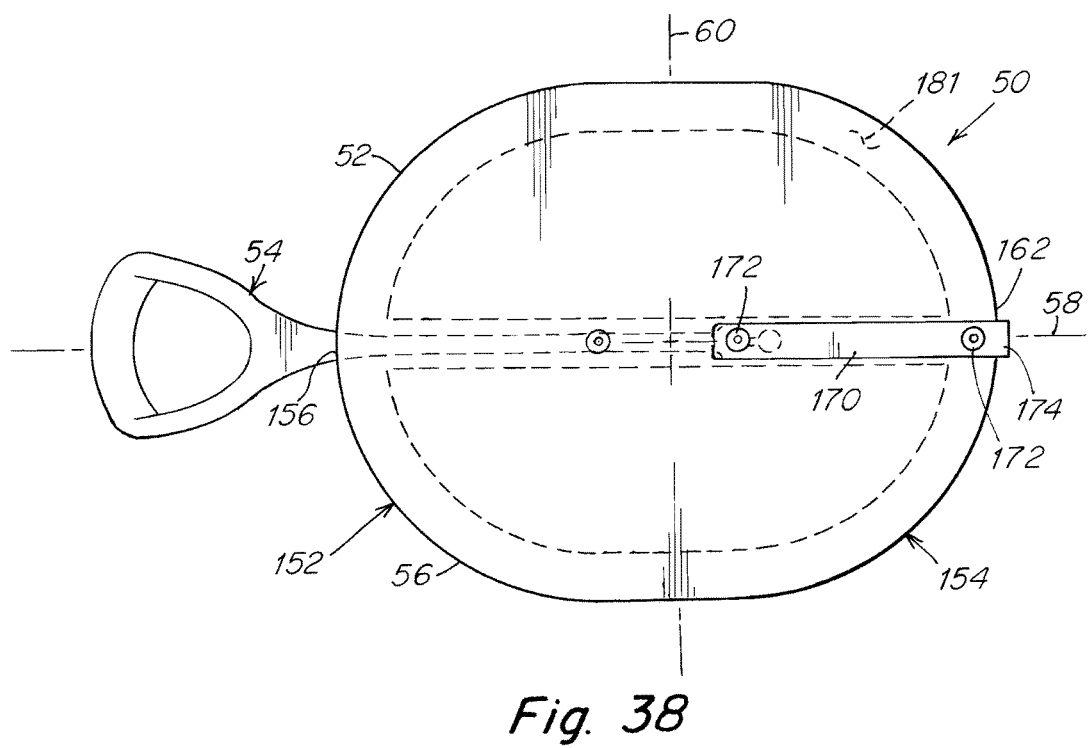
FIG. 38 is a bottom view of the deployment device of FIG. 37.

In one embodiment as shown in FIGS. 37-40, the handle 54 may include a handle pull 169 that extends from a location outside the outer peripheral edge at the second end of the support body. The handle 54 may include a handle base 170 for mounting the handle pull 169 to the support body. The handle base may be configured as a force translation component to translate the pulling force across a region of the support body from the outer peripheral edge at the second end 162 toward the second axis 60 of the support body. As shown in FIG. 38, the handle base 170 may be located along the first axis 58 adjacent the second side of the support body opposite the handle 54 so that a pulling force on the handle is applied in an outward direction away from the first side of the support body and against the second side of the support body. The handle base 170 may have an elongated configuration extending from a location proximate the second axis 60 to a location adjacent the peripheral edge 56. The handle base may be attached to the support body using fasteners 172, including rivets or screws, or otherwise secured, such as by welding or bonding with an adhesive, as should be apparent to one of skill in the art.

The handle pull 169 may extend from an end 174 of the handle base 170 extending beyond the outer peripheral edge 56 at the second end 162 of the support body. The handle pull 169 and the handle base 170 may be integrally formed as a single structure with an integral hinge 176, such as a living hinge, or other pivoting feature coupling the handle pull to the handle base. Alternatively, the handle pull and the handle base may be separately fabricated components coupled together with a separate hinge or otherwise fastened to each other using any suitable arrangement as should be apparent to one of skill in the art.

An arrangement having the handle extending from a location adjacent the outer peripheral edge of the support body may potentially render positioning and/or manipulation of the support body with the handle difficult. Thus, the deployment device may include one or more features to facilitate manipulation and/or positioning of the patch body relative to the hernia defect.

In one embodiment illustrated in FIGS. 37-38, the deployment device may include a handle fastening arrangement that releasably secures a portion of the handle to the support body at a location that provides sufficient leverage for manipulating and/or positioning the support body and the patch. As shown, the handle pull 169 may include a keyhole opening 171 that is configured to cooperate with the fastener 172 located in proximity to the second axis 60 for attaching the handle base to the support body. In this manner, the handle is effectively coupled to the central region of the support body when the keyhole opening is placed over the fastener such that forces applied with the handle will be transferred to the central region of the support body. When the patch has been positioned, the handle pull 169 may be pulled to release the fastener 172 from the keyhole opening 171 so that the handle can then be lifted and used to withdraw the support body from the patch by applying force at the second end 162 of the support body, as described above.

Additionally or alternatively, the deployment device may include one or more grips 180 extendable away from the support body. Each grip 180 may have a size and/or configuration conducive for being grasped and manipulated by hand and/or surgical tool. Each grip may include one or more features configured to enhance a surgeon's ability to grasp and manipulate the deployment device and associated patch body into position at the treatment site. As shown, each grip 180 may have an annular configuration to enhance the ability for a user to grasp the grip. Additionally or alternatively, other grip configurations and/or features may be employed as should be apparent to one of skill in the art.

Each grip 180 may be movable relative to the support body to facilitate manipulation of the patch body and the support body into the reduced configuration for insertion through a surgical opening into a patient. For example, and without limitation, each grip may be foldable, pivotal or flexible relative to the support body.

Each grip may 180 be centrally located on the support body. As shown, a pair of grips 180 may be located along the second axis 60 of the support body and on opposite sides of the first axis 58. However, any suitable grip arrangement may be employed as should be apparent to one of skill in the art. For example, and without limitation, the grips may be located between the second end 162 and the second axis 60 of the support body.

Figure 39:
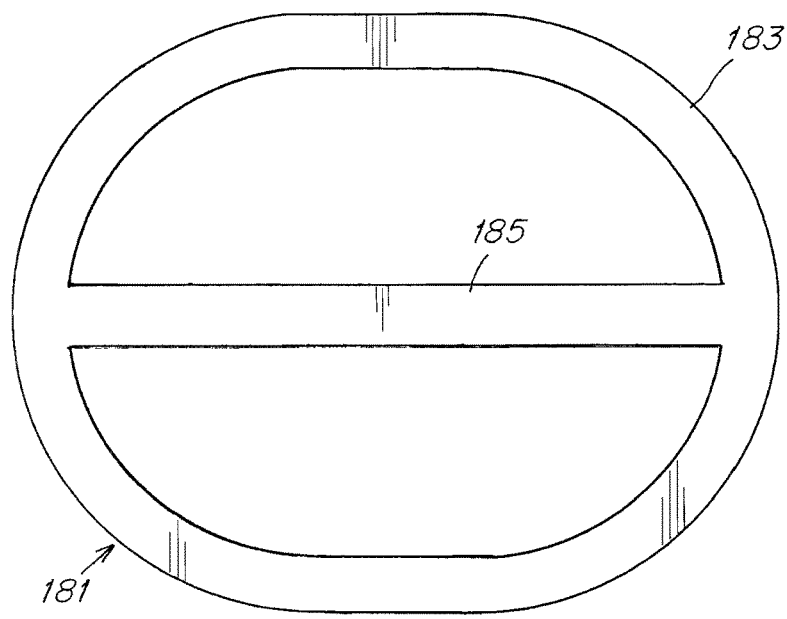
FIG. 39 is an illustration of an embodiment of a support member for the support body of the deployment device of FIGS. 37-38.

In one embodiment, the support body 52 may include a resilient support member to help deploy the support body, and thereby the patch, into an expanded configuration, such as a planar configuration. As illustrated in FIG. 39, the resilient support member 181 may include a frame structure with an outer portion 183 configured to extend along the outer margin of the support body and an inner portion 185 configured to extend along the first axis 58 of the support body. The outer portion 183 may be configured as a continuous loop or ring that extends along the outer margin of the support body. As shown in FIGS. 37-38, the support member 181 may be positioned at the outer peripheral edge 56 of the support segment. However, the support member may be spaced inwardly from the outer peripheral edge and/or at discrete locations throughout the body of the support segment as should be apparent to one of skill in the art. As also shown in FIGS. 37-38, the handle base 170 may be attached to the inner portion of the support member.

As illustrated, the outer portion 183 of the support member may have an annular configuration and the inner portion 185 may have an elongated configuration that extends from the first end 156 to the second end 162 of the support body. Each portion of the support member may have a selected width and thickness to provide a desired degree of resilience or rigidity. The outer portion of the support member may have a generally oval configuration that corresponds to the shape of the support body. However, the support member may have any suitable shape and/or cross section as should be apparent to one of skill in the art.

Figure 40:
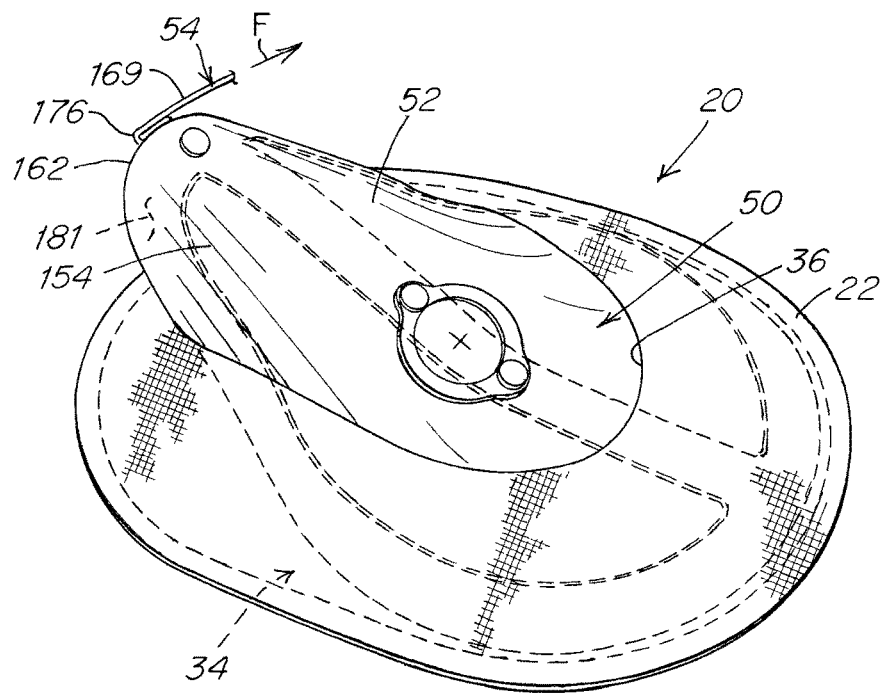
FIG. 40 is an illustration of the deployment device of FIGS. 37-38 being collapsed to a reduced configuration during withdrawal from the pocket of a hernia repair patch.
Figure 41:
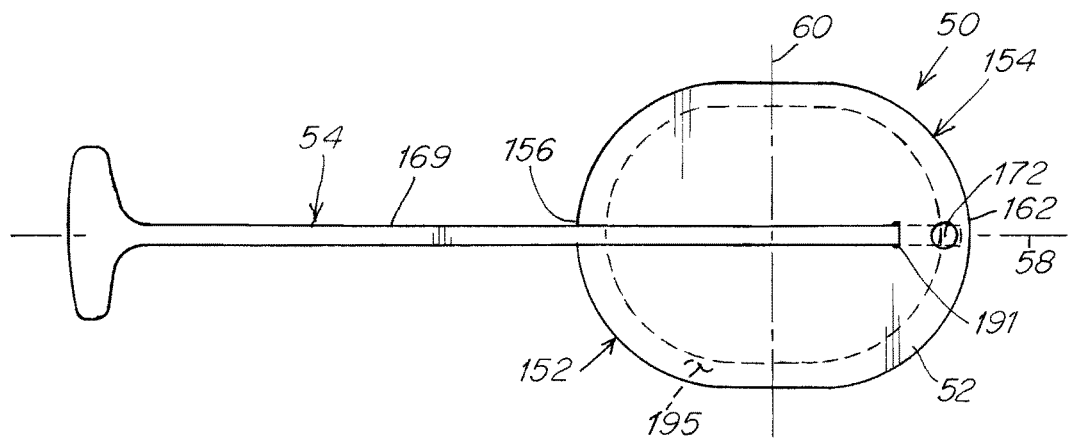
FIG. 41 is an illustration of another embodiment of a deployment device.
Figure 42:
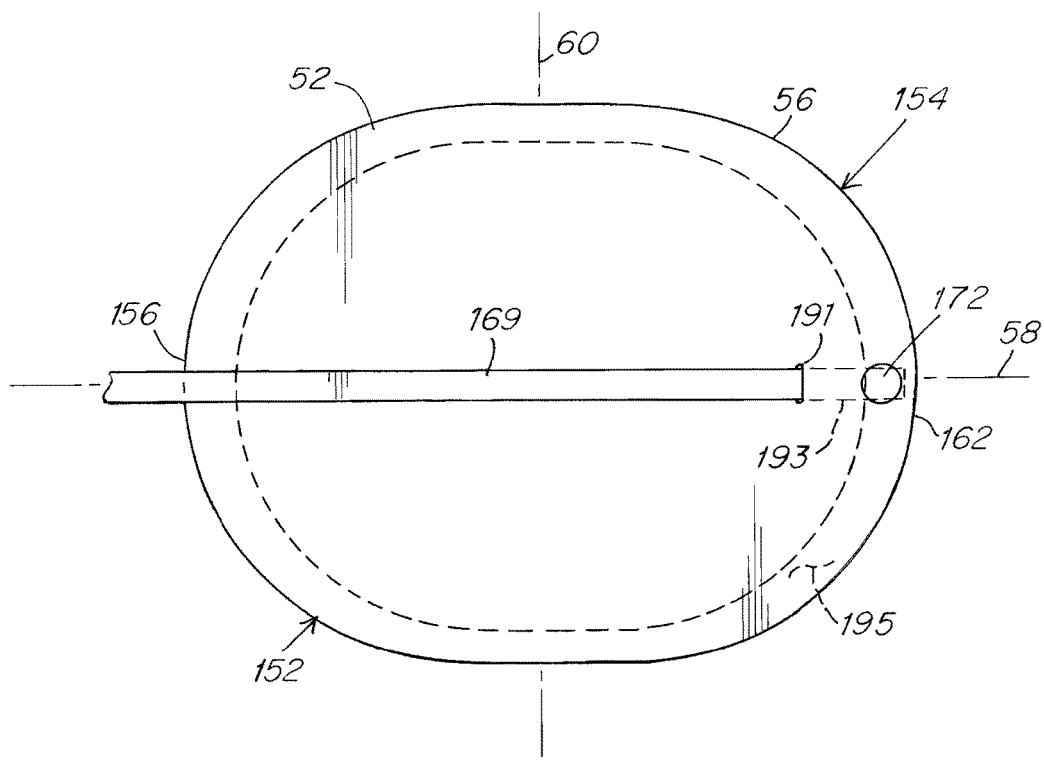
FIG. 42 is an enlarged top view of the support body of the deployment device of FIG. 41.
Figure 43:
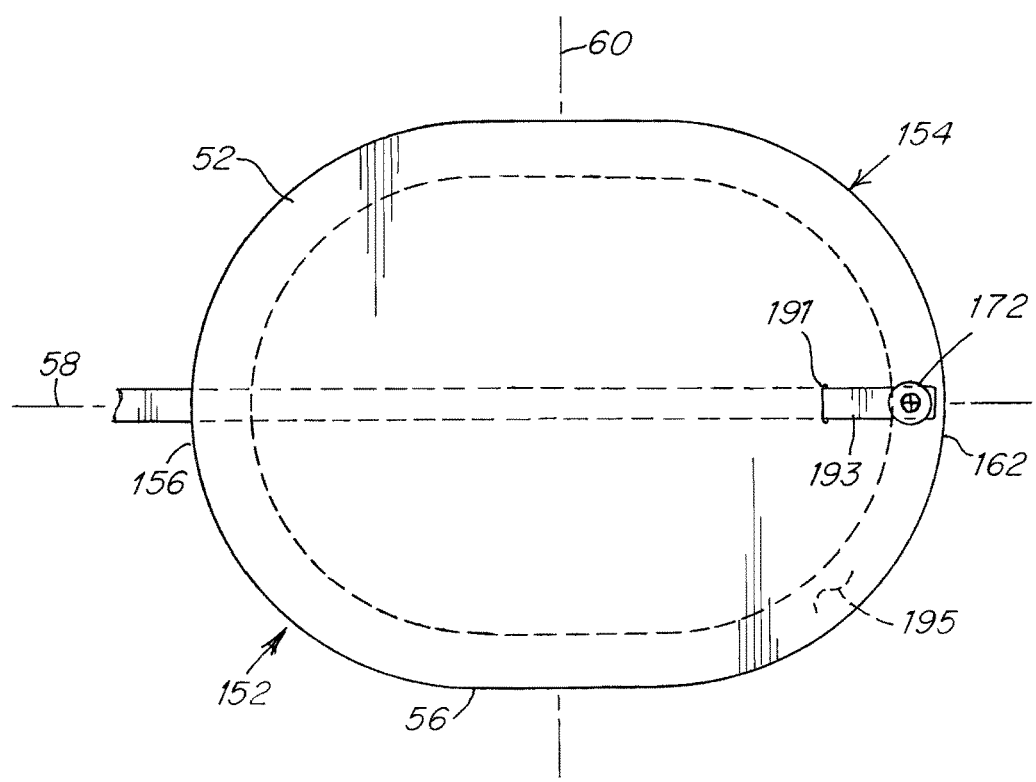
FIG. 43 is a bottom view of the support body of the deployment device of FIGS. 41-42.

Applying a pulling force F on the handle, as illustrated in FIG. 40, encourages the support body 52 to pivot and fold into a reduced configuration, such as a non-planar configuration. As illustrated, pulling the handle 54 in an outward direction away from the patch body 22 draws the second end 162 of the support body in an outward direction away from the patch body. Directing the pulling force toward the outer peripheral edge at the second end of the support body causes at least a segment of the second portion 154 to lift and pivot about a region generally parallel to the second axis 60 while also folding about the first axis 58 as the support body is withdrawn through the access opening 36 of the pocket. Such an arrangement may reduce the pulling force required to remove the deployment device from the pocket of the patch body with minimal, if any, spraying of bodily fluids resulting from the deployment device being withdrawn from the surgical site.

For some applications, rather than lifting the second end of the support body in an upward direction as described above, it may be desirable to pull the second end of the support body in a downward direction to be tucked below the support body as the handle is pulling the support body upwardly away from the patch body. Such an arrangement, if desired, may help reduce the amount of drag and pulling force associated with withdrawing the support body from the patch pocket.

In one embodiment as shown in FIGS. 41-49, the handle 54 may include a handle pull 169 that extends through a region of the second portion 154 of the support body 52 located inward from the second end 162 of the support body. The support body may include a passage 191, such as a hole, slot, or other suitable opening, for permitting a distal portion 193 of the handle pull to pass through the support body. The distal portion 193 of the handle pull may be located along the first axis 58 adjacent the second side of the support body with the remainder of the handle pull located along the first axis but adjacent the first side of the support body. In this manner, the deployment device employs an over-under arrangement for the handle.

As shown, the handle 54 may be arranged to extend along the first axis 58 toward the first end 156 of the support body. The handle pull 169 may be attached to the support body adjacent the second end 162 using a fastener 172, including a rivet or screw, or otherwise secured, such as by welding or bonding with an adhesive, as should be apparent to one of skill in the art.

In one embodiment as shown in FIGS. 41-44, the support body may include a resilient support member 195 to help deploy the support body, and thereby the patch, into an expanded configuration, such as a planar configuration. As illustrated, the resilient support member 195 may include a frame structure configured to extend along the outer margin of the support body. The support member 195 may be configured as a continuous loop or ring that extends along the outer margin of the support body. As shown, the support member may be positioned at the outer peripheral edge 56 of the support segment. However, the support member may be spaced inwardly from the outer peripheral edge and/or at discrete locations throughout the body of the support segment as should be apparent to one of skill in the art.

Figure 44:
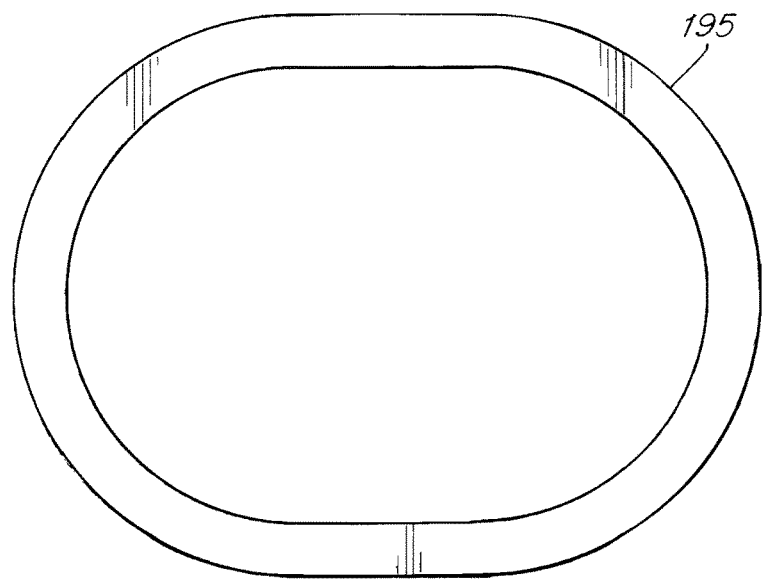
FIG. 44 is an illustration of an embodiment of a support member for the support body of the deployment device of FIGS. 41-43.

As illustrated, the support member 195 may have an annular configuration. The support member may have a selected width and thickness to provide a desired degree of resilience or rigidity. As shown in FIG. 44, the support member 195 may have a generally oval configuration that corresponds to the shape of the support body. However, the support member may have any suitable shape and/or cross section as should be apparent to one of skill in the art.

Rather than using a separate support member, it may be desirable to construct the support body from a single sheet of material that alone provides the desired amount of flexibility, foldability, rollability, resiliency and support. Such an arrangement may reduce costs associated with fabricating and/or assembling the support body.

Figure 45:
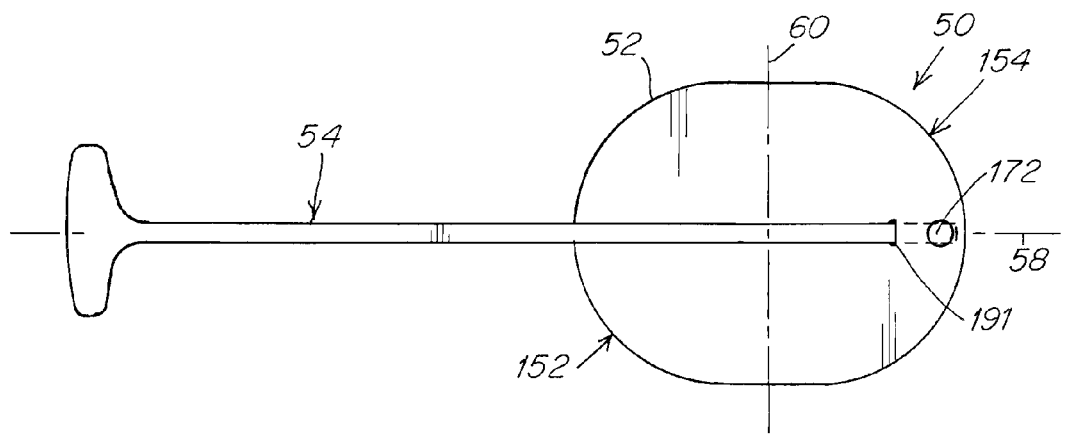
FIG. 45 is an illustration of another embodiment of a deployment device.
Figure 46:
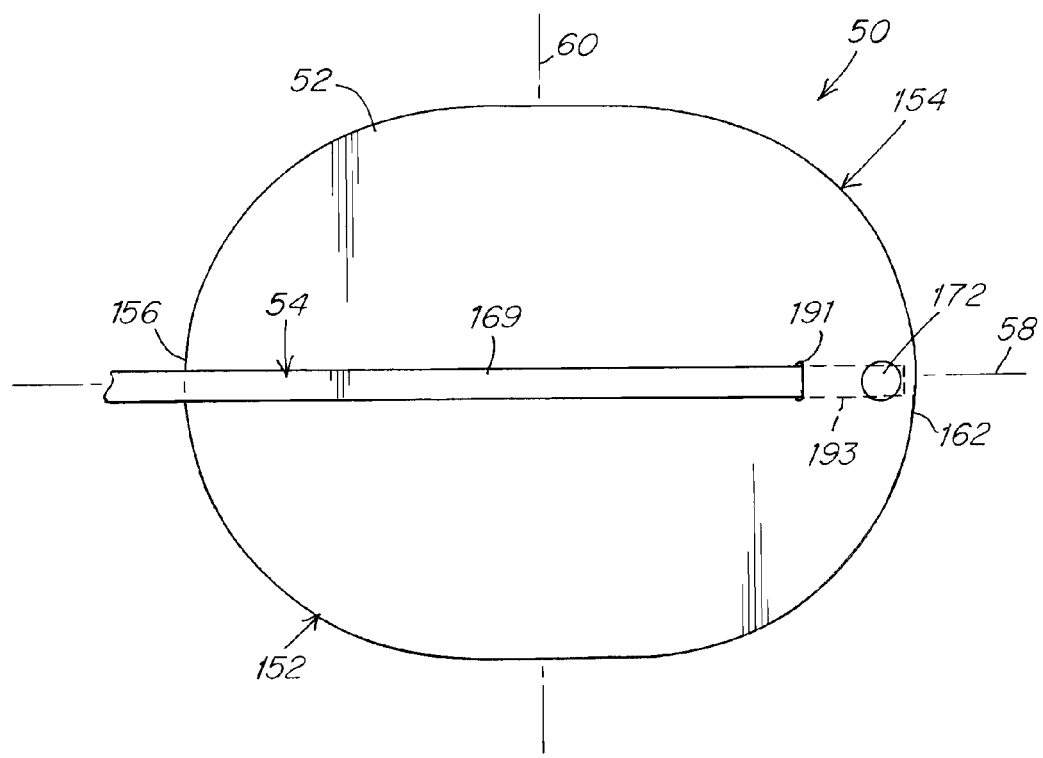
FIG. 46 is an enlarged top view of the support body of the deployment device of FIG. 45.
Figure 47:
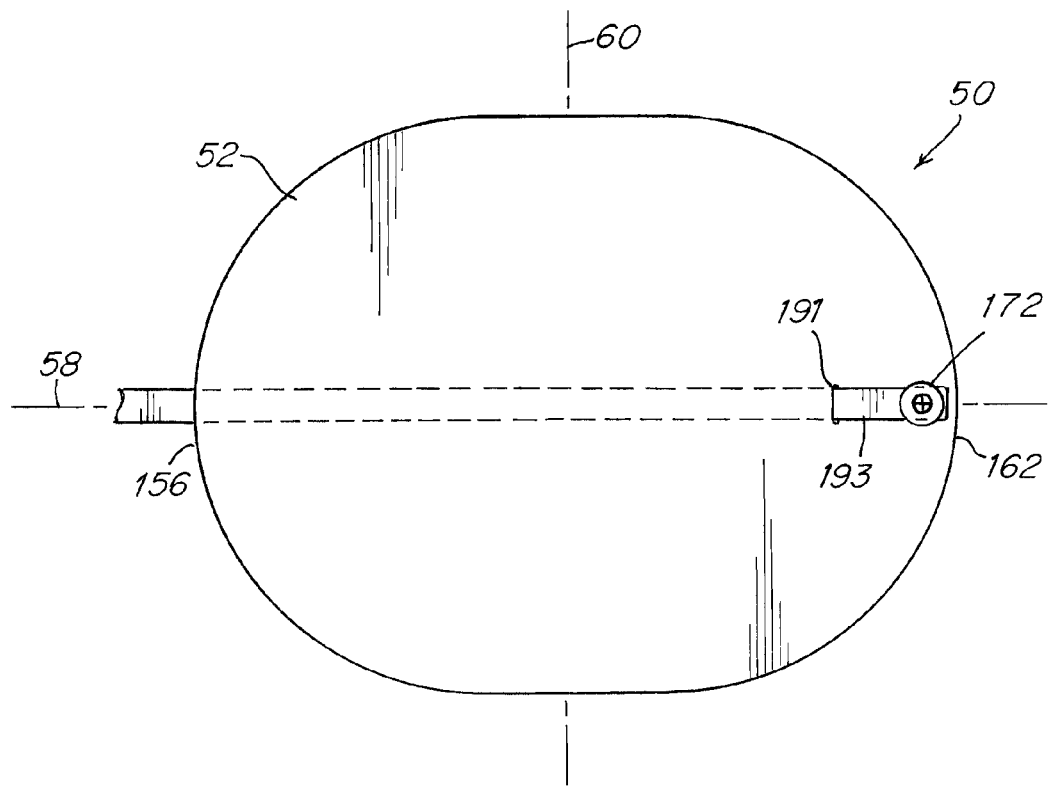
FIG. 47 is a bottom view of the support body of the deployment device of FIGS. 45-46.

As shown in FIGS. 45-47, the support body 52 may be formed from a sheet of material that alone provides a desired balance of flexibility, stiffness and resilience for allowing the support body to be collapsed and expanded while providing support for the patch. For example and without limitation, the support body may be fabricated from a sheet of plastic material that provides the support body with the desired support properties, as well as other properties including, but not limited to, strength and/or stress crack resistance.

Any of the deployment devices of FIGS. 41-47 may include one or more grips and/or a handle fastening arrangement that releasably secures a portion of the handle to the support body at a location that provides sufficient leverage for manipulating and/or positioning the support body and the patch. In one embodiment, the deployment devices may employ grips and/or a handle fastening arrangement as described above in connection with FIGS. 37-38.

Figure 48:
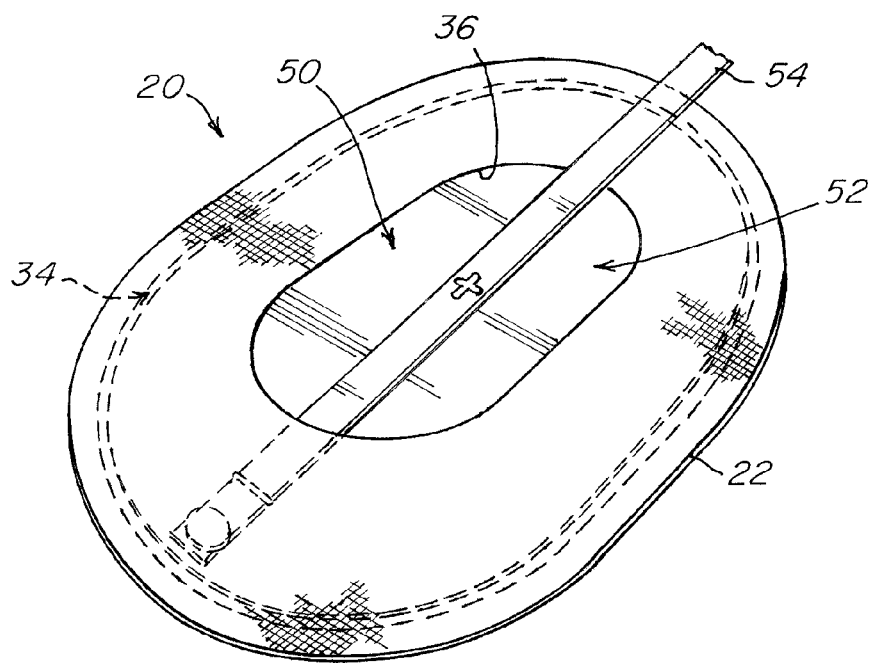
FIG. 48 is an illustration of a prosthesis for repairing a hernia defect with an assembled hernia repair patch and deployment device of FIGS. 45-47 in an expanded configuration.
Figure 49:
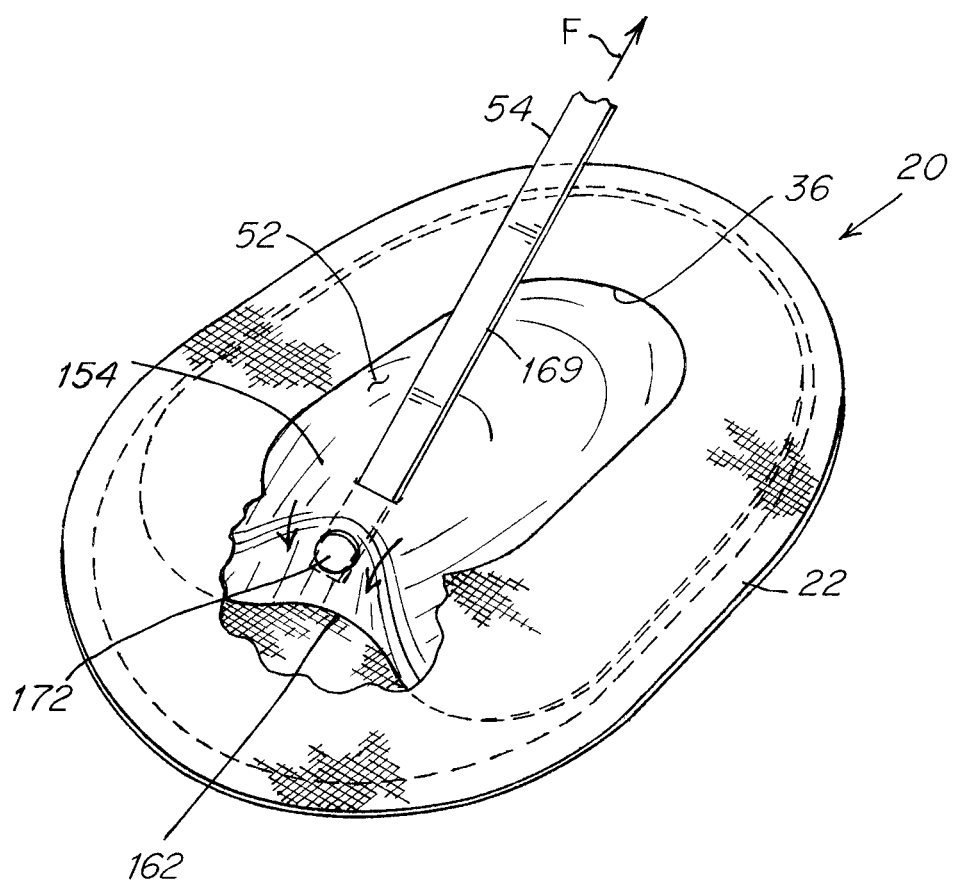
FIG. 49 is an illustration of the deployment device of FIGS. 45-47 being collapsed to a reduced configuration during withdrawal from the pocket of the hernia repair patch.

Applying a pulling force F on the handle pull 54, as illustrated in FIGS. 48-49, encourages the support body 52 to pivot and fold into a reduced configuration, such as a non-planar configuration. As shown in FIG. 49, pulling the handle in an outward direction away from the patch body pulls the second end 162 of the support body downwardly toward the patch body 22 and toward the second axis 60 of the support body causing the second portion 154 of the support body to fold, bend, roll or otherwise collapse inwardly and become tucked below the second side of the support body. The outward pulling force F on the handle also causes at least a segment of the second portion 154 to lift and pivot about a region generally parallel to the second axis 60 while also folding about the first axis 58 as the support body is withdrawn through the access opening 36 of the pocket.

Such an arrangement may reduce the pulling force required to remove the deployment device from the pocket of the patch body with minimal, if any, spraying of bodily fluids resulting from the deployment device being withdrawn from the surgical site.

In several embodiments described above, the support body 52 and/or the support segments 66, 68 may include a resilient support member to help deploy the support body, and thereby the patch, into an expanded configuration. The stiffness or rigidity of the support member may be varied depending on the amount of collapsibility and support desired for the support body.

In one embodiment, the support member(s) may be formed from a sheet of medical grade polyethylene terephthalate glycol (PETG) having a thickness of 0.015 inches, such as available from Pacur LLC of Oshkosh Wis. The material may be laser cut into the desired configuration having an annular width of 1 cm along the entire length of the support member. However, the thickness and/or width of the support member or portions of the support member may be varied to provide a desired degree of resilience or rigidity. For example, and without limitation, the support member may have a width of 0.5 cm to 2 cm. The width may be constant along the entire support member or different portions of the support member may have different widths and/or thicknesses. For example, and without limitation, the center portion of the support member may have a width that differs from the width of the outer portion. However, the support member(s) may be fabricated from any suitable material, including shape memory materials such as Nitinol, which provides a desired balance of flexibility, stiffness and resilience for allowing the support body to be collapsed and expanded while providing support for the patch as should be apparent to one of skill in the art.

In one embodiment, the support member may be sandwiched between two layers of flexible material and may or may not be physically attached thereto. The layers of flexible material may help protect underlying tissue and/or adjacent sensitive organs, such as the intestines or other viscera, from unintentional penetration by the fixation elements during fixation of the patch about the hernia defect. When inserted into the pocket, a surgical instrument may be moved along a surface of the support body into position for delivering a fixation element. The support segments may be constructed of material that is difficult to penetrate with fixation tools and fixation elements. The material of the support segments may also have a lubricity that facilitates sliding a fixation tool along the surface into position, as well as facilitate insertion and withdrawal of the support body into and from the patch.

In one embodiment, the support body or support segments may include two layers of 30 Denier ripstop nylon coated with a 0.003 inch thermoplastic urethane, such as available from Brookwood Companies, Inc. of New York, N.Y. The support member(s) may be laminated with the layers of nylon material. For example, a support member may be placed between the layers of material with the urethane coating of each layer facing inwardly towards the support member. The stack of materials may then be placed between stainless steel shims that are rolled through a standard desk-top laminator to join the materials together. However, the support member may be coupled to the support segment in any suitable manner as should be apparent to one of skill in the art. For example, and without limitation, the support member may be tightly or loosely held within a channel formed by a pair of seams joining the layers of material together, such as by stitching. Rather than being sandwiched, the support member may overlie or underlie and be attached to a layer of material with stiches or a bonding agent, or be fused with ultrasonic, induction, vibration, infrared/laser welding and the like. Moreover, the layers of the support body may be fabricated from any suitable material that provides a desired amount of flexibility, puncture resistance and/or lubricity as should be apparent to one of skill in the art.

In several embodiments described above, the support body 52 and/or the support segments 66, 68 may be formed from a sheet of material that alone provides a desired balance of flexibility, stiffness and resilience for allowing the support body to be collapsed and expanded while providing support for the patch. For example, the support body may be formed from one or more sheets of plastic material including, but not limited to, polytetrafluoroethylene (PTFE), polypropylene, polyethylene, and polyethylene terephthalate glycol (PETG). It is also contemplated that the support body may be formed of an elastomeric material including, but not limited to, silicone. When formed of an elastomeric material, the support body may have sufficient flexibility such that preformed features may be unnecessary to facilitate folding, bending or flexing.

In one embodiment, the support body and/or each support segment may include a laminated sheet formed from multiple layers of polytetrafluoroethylene (PTFE) material. The number, thickness and/or orientation of individual layers relative to each other may be selected to provide the laminated sheet with desired properties for flexibility, stiffness and/or resilience, as well as multidirectional strength and stress crack resistance. The PTFE material may also provide lubricity that may facilitate insertion and withdrawal of the support segments into and from the patch pocket, as well as facilitate movement of a fixation device along the surface of the support segments. The material may be cut to the desired configuration for the support body and/or the support segments.

In one embodiment, the support body and/or the support segments may be fabricated from a sheet of CROSSFILM material, which is a laminated sheet of PTFE, available from Textile Coated International of Manchester, N.H. The material may have a thickness of 0.012 inches to 0.020 inches. However, the support body and/or the support segments may be fabricated from any suitable material that provides a desired balance of flexibility, stiffness and resilience for allowing the support body to be collapsed and expanded while providing support for the patch as should be apparent to one of skill in the art.

The handle may be formed of a plastic material including, but not limited to, polypropylene, polyethylene and polytetrafluoroethylene (PTFE), that provides the desired level of stiffness, flexibility, foldability and rollability suitable for a particular application. In one embodiment, the handle may be formed from a polypropylene material having a thickness of 0.030 inches, such as FORMEX GK-30BK available from ESPE Manufacturing Co. of Schiller Park, Ill. The handle may be laser cut to the desired configuration from a sheet of the material. However, the handle may be formed from any suitable material using any suitable fabrication process as should be apparent to one of skill in the art.

Various techniques may be employed to reduce the assembled patch and deployment device to a smaller configuration suitable for delivery through an opening, such as a surgical incision. For example, and without limitation, the assembled patch and deployment device may be rolled up into a cylinder. In one embodiment, the assembled patch and deployment device may be rolled by hand about an axis generally parallel to the first axis with the handle pull positioned along the first axis and the handle base positioned along the second axis. For example, one edge of the patch body intersected by the second axis may be rolled in a direction along the second axis toward the opposite edge of the patch body intersected by the second axis.

The patch body 22 may have any form appropriate for repairing a hernia defect. The patch may be substantially flat or may be arranged with a concave, convex, or a combination concave/convex surface. The distance between edges of the patch body along the first axis 28 may be greater than the distance between edges of the patch body along the second axis 30; that is, the patch body may be elongated along the first axis. The shape of the patch body when viewed along the first axis may be different than the shape of the patch body when viewed along the second axis. For example, and without limitation, the edges of the patch body intersected by the first axis may be generally round while the edges of the patch body intersected by the second axis may be linear and run parallel to the first axis. Other patch body configurations are contemplated as should be apparent to one of skill in the art.

The patch body 22 may be formed of a porous material, such as a knit fabric, woven or non-woven fabric, or may be composed of a solid, substantially non-porous, or microporous material. The patch body may be formed of one or more layers of the same or dissimilar material, and the layers may be stacked one on top of the other, side-to-side, or include a combination of both stacking arrangements. The patch body may be formed with portions that are tissue infiltratable and other portions that are less tissue infiltratable or are non-tissue infiltratable, providing selected areas of the repair device with different tissue ingrowth and adhesion resistant properties. The patch body may be formed of permanent material, resorbable material, or a combination of permanent and resorbable materials. It should be appreciated that the patch body may be formed of any biologically compatible material, synthetic or natural, suitable for repairing a tissue or muscle wall defect as would be apparent to one of skill in the art.

A representative embodiment of the hernia repair patch and a representative procedure for using same is now described. A hernia repair patch configured to repair a ventral hernia includes a patch body having a tissue infiltratable layer on one side and a barrier layer on the other side. The tissue infiltratable layer may include one or more sheets of surgical mesh fabric, such as a polypropylene knit. The barrier layer may be a sheet of synthetic or natural barrier material; for example, and without limitation, a sheet of ePTFE may be stitched, heat fused or otherwise connected to a polypropylene sheet. Another option is to embed the polypropylene knit into a film of SEPRA (bioresorbable hydrogel barrier). The polypropylene side would face the abdominal wall and the ePTFE or SEPRA side would face the viscera.

A flat, generally oval-shaped, support body includes first and second support segments coupled to a handle base at hinge points located along the second axis of the support body. A handle pull is pivotally coupled to the handle base and is located at the approximate center of the support body. The support body is configured to collapse for insertion into and withdrawal from a pocket in the patch body. The support body has a generally oval shape that corresponds to the shape and occupies a substantial portion of the pocket.

The center of the support body is registered with the center of the patch body, with the outer peripheral edge of the support body generally following the periphery of the pocket of the patch body. The support body is collapsed from a planar, expanded configuration larger than the access opening to a non-planar configuration smaller than the access opening for insertion into the pocket of the patch body. Thereafter, the support body is opened to the expanded configuration within the pocket, securing the patch body to the deployment device. The handle pull extends through the access opening and out beyond the tissue infiltratable side where it will be accessible for manipulation to hoist the support body and associated patch body against the abdominal wall.

The flexible patch and deployment device are rolled into a reduced configuration and then delivered through an opening, such as an incision, into a patient. Upon exiting the incision, the support body returns to a larger shape, spreading the patch body into an expanded configuration. The handle pull extending from the patch may be pulled through the incision in the abdominal wall and then manipulated outside of the patient to hoist the support body and assembled patch body against the abdominal wall about the defect. With the patch positioned against the abdominal wall, fixation elements, such as a suture, tack, or staple, are delivered through the pocket and applied through the periphery of the patch adjacent the pocket and, or if desired, through the central opening in the support body.

With the patch securely fixated to the abdominal wall, the deployment device may then be removed from the anchored patch. For example, the surgical team may use the handle pull to grip and pull the support body out of the pocket and away from the patch. In response to the pulling force, the support body and the handle base, if so configured, collapse by pivoting and folding of the support segments and transform to a collapsed configuration (e.g., generally flattened trapezoidal) allowing the support body to slide through the access opening of the patch body. Once separated from the patch, the support body may be withdrawn through the same opening, such as a surgical incision, via which the assembled deployment device and patch were originally delivered to the surgical site. The collapsed deployment device may be removed from the treatment site with minimal, if any, splashing of bodily fluids.

For purposes of this patent application and any patent issuing thereon, the indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

The foregoing description of various embodiments are intended merely to be illustrative thereof and that other embodiments, modifications, and equivalents are within the scope of the invention recited in the claims appended hereto.

What is claimed is:

1. A deployment device for a soft tissue repair prosthesis, the deployment device comprising:
    a self-expanding support body to be releasably coupled to the soft tissue repair prosthesis to assist in spreading the soft tissue repair prosthesis from a reduced configuration to an expanded configuration, the support body including an outer periphery, a first side and a second side opposite the first side, the support body being collapsible from an expanded configuration to a reduced configuration; and
    a handle including a distal end and a free end opposite the distal end, the distal end of the handle coupled to the support body to position the soft tissue repair prosthesis relative to a soft tissue defect when the support body is coupled to the soft tissue repair prosthesis and to release the support body from the soft tissue repair prosthesis with a pulling force on the free end of the handle in an outward direction away from the soft tissue repair prosthesis when the soft tissue repair prosthesis is in the expanded configuration, the distal end of the handle being coupled to a portion of the support body proximate to the outer periphery to apply the pulling force with the free end of the handle from above the first side and cause the portion of the support body to collapse in an inward direction toward the soft tissue repair prosthesis and become tucked below the second side,
    wherein the support body is manipulable into the reduced configuration with the soft tissue repair prosthesis for insertion through a surgical opening into a patient.

2. The deployment device according to claim 1, wherein the expanded configuration of the support body has a planar configuration and the reduced configuration of the support body has a non-planar configuration.

3. The deployment device according to claim 1, wherein the support body is formed as a single piece structure.

4. The deployment device according to claim 1, wherein the support body includes a resilient support member to support the support body in the expanded configuration.

5. The deployment device according to claim 4, wherein the resilient support member extends along the outer periphery of the support body.

6. The deployment device according to claim 1, wherein the support body has a first axis and a second axis perpendicular to the first axis, the first axis and the second axis intersecting at approximately a center of the support body, the support body including first and second portions on opposite sides of the second axis, the handle being coupled to the second portion of the support body along the first axis.

7. The deployment device according to claim 6, wherein the handle extends in a direction parallel to the first axis.

8. The deployment device according to claim 6, wherein the handle is located along the first axis.

9. The deployment device according to claim 6, wherein the handle extends through the second portion of the support body.

10. The deployment device according to claim 9, wherein a first portion of the handle is located adjacent the first side of the support body and a second portion of the handle being located adjacent the second side of the support body.

11. The deployment device according to claim 1, wherein the soft tissue repair prosthesis comprises a patch body including a pocket and an access opening configured to provide access to the pocket, wherein the support body is configured to be removably inserted into the pocket through the access opening to assist in spreading the patch body from the reduced configuration to the expanded configuration, the support body being insertable into and removable from the pocket when collapsed from the expanded configuration to the reduced configuration, and wherein the free end of the handle is extendable away from the support body and through the access opening when the support body is removably inserted in the pocket of the patch body, the support body being removable from the pocket with a pulling force on the free end of the handle in an outward direction away from the patch body when the patch body is in the expanded configuration.

12. The deployment device according to claim 11, in combination with the soft tissue repair prosthesis.

13. The deployment device in combination with the soft tissue repair prosthesis according to claim 12, wherein the patch body includes first and second layers attached together to form the pocket therebetween, one of the first and second layers including the access opening therethrough to provide access to the pocket.

14. The deployment device in combination with the soft tissue repair prosthesis according to claim 12, wherein the pocket has an outer periphery and the support body includes an outer peripheral edge along the outer periphery thereof, the outer peripheral edge of the support body configured to follow the outer periphery of the pocket.

15. The deployment device in combination with the soft tissue repair prosthesis according to claim 12, wherein the support body is configured to substantially occupy the pocket.

* * * * *